United States Patent
Skardal et al.

(10) Patent No.: US 11,959,095 B2
(45) Date of Patent: Apr. 16, 2024

(54) COMPOSITIONS, CELL CONSTRUCTS, AND METHODS OF MAKING AND USING THE SAME

(71) Applicant: Wake Forest University Health Sciences, Winston-Salem, NC (US)

(72) Inventors: Aleksander Skardal, Clemmons, NC (US); HemaMylammal Salem Muthu Sugavanam Sivakumar, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 376 days.

(21) Appl. No.: 16/341,525

(22) PCT Filed: Oct. 13, 2017

(86) PCT No.: PCT/US2017/056558
§ 371 (c)(1),
(2) Date: Apr. 12, 2019

(87) PCT Pub. No.: WO2018/071797
PCT Pub. Date: Apr. 19, 2018

(65) Prior Publication Data
US 2019/0345439 A1    Nov. 14, 2019

Related U.S. Application Data

(60) Provisional application No. 62/408,119, filed on Oct. 14, 2016.

(51) Int. Cl.
*C12N 5/071* (2010.01)
*C12N 5/00* (2006.01)
*C12N 5/079* (2010.01)
*C12N 5/09* (2010.01)
*G01N 33/50* (2006.01)

(52) U.S. Cl.
CPC ......... *C12N 5/0068* (2013.01); *C12N 5/0622* (2013.01); *C12N 5/067* (2013.01); *C12N 5/0693* (2013.01); *G01N 33/502* (2013.01); *C12N 2503/02* (2013.01); *C12N 2503/04* (2013.01); *C12N 2513/00* (2013.01); *C12N 2533/54* (2013.01); *C12N 2533/80* (2013.01); *C12N 2533/90* (2013.01); *C12N 2537/10* (2013.01); *C12Y 302/01035* (2013.01); *G01N 2800/52* (2013.01)

(58) Field of Classification Search
CPC .... C12N 5/0068; C12N 5/0622; C12N 5/067; C12N 5/0693; C12N 2503/02; C12N 2503/04; C12N 2513/00; C12N 2533/54; C12N 2533/80; C12N 2533/90; C12N 2537/10; G01N 33/502; G01N 2800/52; C12Y 302/01035; C12Y 304/24007
See application file for complete search history.

(56) References Cited

U.S. PATENT DOCUMENTS

| | | | | |
|---|---|---|---|---|
| 2003/0088885 A1* | 5/2003 | Yang | ................... | A61K 49/0008 435/6.16 |
| 2007/0087435 A1* | 4/2007 | Skorecki | ............... | C12N 5/0693 435/456 |
| 2012/0089238 A1 | 4/2012 | Kang et al. | | |
| 2012/0114670 A1 | 5/2012 | Land et al. | | |
| 2014/0154735 A1* | 6/2014 | Sundstrom | ......... | G01N 33/5011 435/373 |
| 2015/0082468 A1 | 3/2015 | Bhatia et al. | | |
| 2017/0107483 A1 | 4/2017 | Pendergraft et al. | | |
| 2017/0307598 A1 | 10/2017 | Skardal et al. | | |
| 2018/0000743 A1 | 1/2018 | Welker et al. | | |
| 2018/0273904 A1 | 9/2018 | Skardal et al. | | |
| 2018/0291350 A1 | 10/2018 | Murphy et al. | | |

(Continued)

FOREIGN PATENT DOCUMENTS

| | | | | |
|---|---|---|---|---|
| WO | WO 00/75286 | * 12/2000 | ............... | C12N 5/00 |
| WO | 2018004906 | 1/2018 | | |

(Continued)

OTHER PUBLICATIONS

Hubert et al. A Three-Dimensional Organoid Culture System Derived from Human Glioblastomas Recapitulates the Hypoxic Gradients and Cancer Stem Cell Heterogeneity of Tumors Found In Vivo. Cancer Res. Apr. 15, 2016;76(8):2465-77. Epub Feb. 19, 2016. (Year: 2016).*

Nguyen DT, Fan Y, Akay YM, Akay M. Investigating Glioblastoma Angiogenesis Using A 3D in Vitro GelMA Microwell Platform. IEEE Trans Nanobioscience. Apr. 2016;15(3):289-93. Epub Mar. 25, 2016. (Year: 2016).*

Vamvakidou AP, Mondrinos MJ, Petushi SP, Garcia FU, Lelkes PI, Tozeren A. Heterogeneous breast tumoroids: An in vitro assay for investigating cellular heterogeneity and drug delivery. J Biomol Screen. Feb. 2007;12(1):13-20. Epub Dec. 8, 2006. (Year: 2006).*

Yang et al. A co-culture model with brain tumor-specific bioluminescence demonstrates astrocyte-induced drug resistance in glioblastoma. J Transl Med. Oct. 4, 2014; 12:278. (Year: 2014).*

(Continued)

*Primary Examiner* — Titilayo Moloye
(74) *Attorney, Agent, or Firm* — Myers Bigel, P.A.

(57) ABSTRACT

An extrudable hydrogel composition useful for making a three-dimensional organ construct is described herein. Methods of using the same and products so made are also described. Also described herein is a multicellular organoid including at least two tumor cells or cell lines that are of the same tissue type, but are distinct from one another (e.g., distinct in morphology, growth rate, and/or at least one mutation); and at least one type of non-cancerous (i.e., normal or differentiated) tissue cells, wherein the at least one type of non-cancerous tissue cells are of the same tissue type as the at least two tumor cells or cell lines. In some embodiments, the at least two tumor cells or cell lines and/or the non-cancerous tissue cells are labeled with and/or comprise a detectable compound, optionally so that each of the different cells can be distinguished from each other (e.g., optically and/or electrically distinguished).

19 Claims, 17 Drawing Sheets

(56) References Cited

U.S. PATENT DOCUMENTS

| | | |
|---|---|---|
| 2018/0320141 A1 | 11/2018 | Atala et al. |
| 2018/0348203 A1 | 12/2018 | Skardal |
| 2019/0106673 A1 | 4/2019 | Skardal |
| 2020/0048601 A1 | 2/2020 | Skardal et al. |
| 2020/0108172 A1 | 4/2020 | Skardal et al. |

FOREIGN PATENT DOCUMENTS

| | | |
|---|---|---|
| WO | 2018005964 | 1/2018 |
| WO | 2018027023 | 2/2018 |
| WO | 2018071354 | 4/2018 |
| WO | 2018081425 | 5/2018 |
| WO | 2019028131 | 2/2019 |
| WO | 2019152767 | 8/2019 |

OTHER PUBLICATIONS

Kharkar PM, Kiick KL, Kloxin AM. Designing degradable hydrogels for orthogonal control of cell microenvironments. Chem Soc Rev. Sep. 7, 2013;42(17):7335-72 Epub Apr. 22, 2013. (Year: 2013).*

Burdick JA, Chung C, Jia X, Randolph MA, Langer R. Controlled degradation and mechanical behavior of photopolymerized hyaluronic acid networks. Biomacromolecules. 2005;6(1):386-391. (Year: 2005).*

Grotzer MA, Neve A, Baumgartner M. Dissecting brain tumor growth and metastasis in vitro and ex vivo. J Cancer Metastasis Treat May 2016;2:149-62. (Year: 2016).*

Pore N, Liu S, Haas-Kogan DA, O'Rourke DM, Maity A. PTEN mutation and epidermal growth factor receptor activation regulate vascular endothelial growth factor (VEGF) mRNA expression in human glioblastoma cells by transactivating the proximal VEGF promoter. Cancer Res. Jan. 1, 2003;63(1):236-41. (Year: 2003).*

Van Meir EG, Kikuchi T, Tada M, Li H, Diserens AC, Wojcik BE, Huang HJ, Friedmann T, de Tribolet N, Cavenee WK. Analysis of the p53 gene and its expression in human glioblastoma cells. Cancer Res. Feb. 1, 1994;54(3):649-52. (Year: 1994).*

Duerr EM, Rollbrocker B, Hayashi Y, Peters N, Meyer-Puttlitz B, Louis DN, Schramm J, Wiestler OD, Parsons R, Eng C, von Deimling A. PTEN mutations in gliomas and glioneuronal tumors. Oncogene. Apr. 30, 1998;16(17):2259-64. (Year: 1998).*

Patel AP, Tirosh I, Trombetta JJ, Shalek AK, Gillespie SM, Wakimoto H, Cahill DP, Nahed BV, Curry WT, Martuza RL, Louis DN, Rozenblatt-Rosen O, Suvà ML, Regev A, Bernstein BE. Single-cell RNA-seq highlights intratumoral heterogeneity in primary glioblastoma. Science. Jun. 20, 2014;344(6190):1396-401. (Year: 2014).*

Ananthanarayanan et al. "Elucidating the mechanobiology of malignant brain tumors using a brain matrix-mimetic hyaluronic acid hydrogel platform." Biomaterials. Nov. 2011; 32(31): 7913-7923. (Year: 2011).*

Liu et al. "Disulfide-crosslinked hyaluronan-gelatin sponge: growth of fibrous tissue in vivo."J Biomed Mater Res A. Jan. 1, 2004;68(1):142-9. (Year: 2004).*

Xu et al. "MRI-localized biopsies reveal subtype-specific differences in molecular and cellular composition at the margins of glioblastoma." J Control Release Oct. 28, 2015;216:47-55 (Year: 2015).*

Gill et al. "MRI-localized biopsies reveal subtype-specific differences in molecular and cellular composition at the margins of glioblastoma." Proc Natl Acad Sci U S A.Aug. 26, 2014;111(34):12550-5. (Year: 2014).*

Lin et al. "Astrocytes protect glioma cells from chemotherapy and upregulate survival genes via gap junctional communication." Mol Med Rep.Feb. 2016;13(2):1329-35. (Year: 2016).*

Motain et al. "Heterogeneous glioblastoma cell cross-talk promotes phenotype alterations and enhanced drug resistance." Oncotarget. 2015; 6:40998-41017. (Year: 2015).*

Patil et al. "Elucidating the cancer-specific genetic alteration spectrum of glioblastoma derived cell lines from whole exome and RNA sequencing." Oncotarget. Dec. 22, 2015; 6(41): 43452-43471. (Year: 2015).*

Rao et al. "Glioblastoma behaviors in three-dimensional collagen-hyaluronan composite hydrogels" Oct. 9, 2013;5(19): 9276-84. (Year: 2013).*

Coniglio et al. "Microglial Stimulation of Glioblastoma Invasion Involves Epidermal Growth Factor Receptor (EGFR) and Colony Stimulating Factor 1 Receptor (CSF-1R) Signaling." Molecular Medicine vol. 18, pp. 519-527 (2012) (Year: 2012).*

Urich et al. "Multicellular self-assembled spheroidal model of the blood brain barrier." Scientific Reports vol. 3, Article No. 1500 (2013) (Year: 2013).*

Nguyen et al. "Investigating Glioblastoma Angiogenesis Using A 3D in Vitro GelMA Microwell Platform." IEEE Trans Nanobioscience. Apr. 2016;15(3):289-93. (Year: 2016).*

Chekhonin et al. "Modeling and immunohistochemical analysis of C6 glioma in vivo" Bulletin of Experimental Biology and Medicine vol. 143, pp. 501-509 (2007) (Year: 2007).*

Edmondson et al. "Three-Dimensional Cell Culture Systems and Their Applications in Drug Discovery and Cell-Based Biosensors" Assay and Drug Development Technologies, 12(4):207-218 (2014).

International Search Report and the Written Opinion of the International Searching Authority corresponding to International Patent Application No. PCT/US2017/056558 (13 pages) (dated Feb. 22, 2018).

Insphero AG "3D InSightTM Human Liver Microtissues" Brochure (2 pages) (2012).

International Preliminary Report on Patentability corresponding to International Patent Application No. PCT/US2017/056558 (9 pages) (dated Apr. 25, 2019).

Sivakumar et al. "An In Vitro Model of Glioblastoma and the Brain Tumor Microenvironment" Poster presented at the International Conference on Biofabrication (1 page) (Oct. 29-31, 2016).

Sivakumar, Hemamylammal "In Vitro Model of Glioblastoma to Study the Effects of Brain Microenvironment and Its Mechanical Properties on Tumor Cells" Thesis Submitted to the Graduate Faculty of Wake Forest University Graduate School of Arts and Sciences (64 pages) (Dec. 2016).

Skardal et al. "Tissue specific synthetic ECM hydrogels for 3-D in vitro maintenance of hepatocyte function" Biomaterials, 33(18):4565-4575 (2012).

Stock et al. "Targets for Anti-metastatic Drug Development" Current Pharmaceutical Design, 19:5127-5134 (2013).

Wang et al. "Bioengineered 3D Brain Tumor Model To Elucidate the Effects of Matrix Stiffness on Glioblastoma Cell Behavior Using PEG-Based Hydrogels" Molecular Pharmaceutics, 11(7):2115-2125 (2014).

Azzarelli et al. "Three-dimensional model of glioblastoma by co-culturing tumor stem cells with human brain organoids" Biology Open, 10(2):bio056416 (2021).

Baubet et al. "MODL-28. Patient-derived, three-dimensional organoid platform for pediatric brain tumor modeling" Neuro-Oncology, 24(Suppl 1):i175 (2022).

Goranci-Buzhala et al. "Rapid and Efficient Invasion Assay of Glioblastoma in Human Brain Organoids" Cell Reports, 31(10):107738 (2020).

Urbaniak et al. "Anti-glioblastoma activity of monensin and its analogs in an organoid model of cancer" Biomedicine & Pharmacotherapy, 153:113440 (2022).

Xu et al. "Opportunities and challenges of glioma organoids" Cell Communication and Signaling, 19(102):1-13 (2021).

* cited by examiner

A.

GROWTH FACTOR AND CYTOKINE COMPOSITIONS

| (pg/mL) | L-ECM | C-ECM | SK-ECM | (pg/mL) | L-ECM | C-ECM | SK-ECM |
|---|---|---|---|---|---|---|---|
| AR | 0 | 50.6 | 33.4 | IGFBP-4 | 0 | 574.3 | 1,135.1 |
| BDNF | 105.6 | 5.8 | 29.1 | IGFBP-6 | 0 | 118.4 | 80.5 |
| bFGF | 6,439.30 | 13.2 | 21.5 | IGF-I | 0 | 34.4 | 0.0 |
| BMP-4 | 0 | 49.0 | 0.0 | INSULIN | 0 | 0.0 | 0.2 |
| BMP-5 | 189,712.70 | 329.0 | 659.9 | MCSF R | 0 | 96.6 | 158.9 |
| BMP-7 | 309.6 | 61.0 | 106.0 | NGF R | 0 | 15.9 | 18.1 |
| β-NGF | 0 | 1.6 | 4.0 | NT-3 | 176.7 | 91.5 | 128.7 |
| EGF | 17.7 | 0.3 | 0.4 | NT-4 | 0 | 58.5 | 61.6 |
| EGF R | 27.3 | 6.9 | 4.5 | OPG | 0 | 19.0 | 28.8 |
| EG-VEGF | 0 | 16.8 | 45.6 | PDGF-AA | 0 | 6.8 | 19.7 |
| FGF-4 | 10,471.60 | 733.6 | 1,022.3 | PlGF | 0 | 3.4 | 4.7 |
| FGF-7 | 115.9 | 29.8 | 55.6 | SCF | 0 | 10.7 | 15.5 |
| GDF-15 | 0 | 1.5 | 1.5 | SCF R | 382.1 | 38.0 | 103.3 |
| GDNF | 0 | 35.5 | 53.2 | TGFα | 0 | 0.0 | 0.4 |
| GH | 100.8 | 63.4 | 42.4 | TGFβ1 | 510.9 | 0.0 | 0.0 |
| HB-EGF | 7.8 | 0.3 | 18.3 | TGFβ3 | 0 | 17.2 | 33.5 |
| HGF | 17.5 | 26.0 | 88.3 | VEGF | 0 | 67.3 | 81.2 |
| IGFBP-1 | 0 | 40.3 | 154.2 | VEGF R2 | 0 | 50.8 | 103.1 |
| IGFBP-2 | 95.5 | 100.6 | 132.5 | VEGF R3 | 0 | 20.8 | 92.6 |
| IGFBP-3 | 0 | 1,158.9 | 1,256.5 | VEGF-D | 0 | 0.0 | 48.8 |

B.

*P<0.05 – CONTROL VS. APAP; # P<0.05 – APAP+NAC VS. APAP.

COMPOSITIONS, CELL CONSTRUCTS, AND METHODS OF MAKING AND USING THE SAME

RELATED APPLICATIONS

This application is a 35 U.S.C. § 371 national phase application of International Application Serial No. PCT/US2017/056558, filed Oct. 13, 2017, which claims the benefit of U.S. Provisional Patent Application Ser. No. 62/408,119, filed Oct. 14, 2016, the disclosure of each of which is incorporated by reference herein in their entirety.

FIELD OF THE INVENTION

The present invention generally relates to compositions including hydrogel "bioink" compositions useful for fabrication of artificial cell and/or tissue constructs; artificial cell and/or tissue constructs; methods of making and/or using the same; and products formed therefrom.

BACKGROUND OF THE INVENTION

Biofabrication technologies have emerged as tissue engineering approaches for building organs and organoids or tissue constructs. The combination of biocompatible materials and rapid prototyping provides a way to address the intricacies needed in viable tissues. One of the hurdles associated with biofabrication is the interfacing between the deposition/fabrication hardware and different types of biomaterials (or "bio-inks") being deposited. Standard hydrogels pose design problems because they are either printed as fluid solutions, limiting mechanical properties, or printed as solid hydrogels and broken up upon the extrusion process. This presents difficulties in producing the desired constructs.

The extracellular matrix (ECM) in brain is very different compared to other tissues in the body. Some major matrix proteins present in connective tissues of other organs are completely absent or minimally present in the brain. Hyaluronic acid is one of the major components of the brain ECM. The brain being very different from other tissues might explain the fact that glioblastomas rarely metastasize outside the brain but aggressively invade the brain.

Cancers arising from the same organ may differ significantly from each other and this phenomenon is known as inter tumor heterogeneity. Cells within a tumor may also differ from each other and this phenomenon is known as intratumor heterogeneity. Different clones arise out of a tumor by chance, but then go on to survive and proliferate by the selection pressure in the tumor environment. Tumor evolution is a poorly understood mechanism in glioblastoma (GBM), but also responsible for the intratumor heterogeneity, which in turn drives tumor progression, infiltrative potential and relapse.

SUMMARY OF THE INVENTION

The materials described herein may address the issues noted above for bio-inks and hydrogels by being extrudable and/or by possessing a post-deposition and/or secondary crosslinking step, which may stabilize and increase the stiffness of the end product (e.g., hydrogel) to match a range of tissue types (e.g., brain ECM). Additionally, these "bio-ink" compositions can be supplemented with biochemical factors derived from tissues that result in a biochemical environment more like that of an in vivo tissue than cells in the biofabricated constructs then experience. These factors—both biochemical and mechanical—can increase the ability to maintain viable cells in culture and/or increase their functionality for the duration of culture.

In view of the foregoing, one aspect of the present invention is directed to an extrudable hydrogel composition (or "bioink") useful for making a three-dimensional construct. The composition comprises:
 (a) a cross-linkable prepolymer;
 (b) a post-deposition crosslinking group (also referred to as a second crosslinking group);
 (c) optionally, but in some embodiments preferably, an initiator that catalyzes the reaction between said prepolymer and said post-deposition crosslinking group;
 (d) live cells (e.g., live animal cells);
 (e) optionally, but in some embodiments preferably, at least one growth factor; and
 (f) optionally, water to balance.

In some embodiments, a hydrogel composition (or "bioink") of the present invention is useful for holding and/or supporting a cell and/or artificial cell construct (e.g., a three-dimensional construct or organoid that is already formed). Some embodiments include seeding or placing a cell and/or artificial cell construct (e.g., organoid) on a hydrogel of the present invention, optionally a hydrogel that is at least partially crosslinked. Additional hydrogel may be provided on and/or around the cell and/or artificial cell construct (e.g., organoid) on the hydrogel. In some embodiments, a hydrogel encapsulates and/or surrounds a cell and/or artificial cell construct (e.g., organoid).

Methods of using the foregoing, and products produced therefrom, are also described herein.

Some embodiments of the invention provide advantages as follows:

Control over biochemical properties. Tissues in the body have complex compositions: Various subpopulations of cells secrete signaling molecules such as growth factors and other cytokines that aid in maintaining viability and function of cells in tissues. Extracellular matrix is comprised of proteins and polymers that provide structure to the tissue and also interact with cell receptors acting as another type of signaling. Additionally, some ECM components bind growth factors (heparin, heparan sulfate) and slowly release them to the cells over time. The combination of these signals varies from tissue to tissue. For example, by providing components specific to a tissue (e.g., the liver or brain) within a hydrogel, the hydrogel may better support the cells (e.g., primary human hepatocytes or glial cells). In some embodiments, by decellularizing a tissue, pulverizing it, and dissolving it, tissue-specific biochemical signals may be provided in a hydrogel to provide tissue-specific biochemical signals from the tissue to cells in 3-D hydrogel constructs.

Control over mechanical properties. Mechanical properties, specifically elastic modulus, are important for two major reasons. First, as has been described in earlier reports, control over the hydrogel bioink stiffness allows for extrusion-based biofabrication using a soft gel, which can then be stiffened afterwards by secondary crosslinking to increase stability. Second, this second crosslinking step can be used to reach elastic modulus levels that are consistent with the target organ type for each individual organoid. For example, we can customize the liver bioinks to reach stiffnesses of about 5 to about 10 kPa, like a native liver, or cardiac bioinks (or microenvironment) to reach stiffnesses of about 10 to about 15 kPa like native cardiac tissue, in theory increasing the ability of these organoids to function in a similar manner to their native tissue counterparts.

Another aspect of the present invention is directed to a multicellular organoid including at least two tumor cells or cell lines that are of the same tissue type, but are distinct from one another (e.g., distinct in morphology, growth rate, and/or at least one mutation); and at least one type of non-cancerous (i.e., normal or differentiated) tissue cells, wherein the at least one type of non-cancerous tissue cells are of the same tissue type as the at least two tumor cells or cell lines. In some embodiments, the at least two tumor cells (e.g., cell types) or cell lines and/or the non-cancerous tissue cells are labeled with and/or comprise a detectable compound, optionally so that each of the different cells can be distinguished from each other (e.g., optically and/or electrically distinguished).

A further aspect of the present invention is directed to an artificial cell construct. The artificial cell construct may be useful for screening antitumor agents. The artificial cell construct may include, in combination: (a) a non-natural hydrogel; (b) a first tumor cell or cell line in said hydrogel; (c) a second tumor cell or cell line in said hydrogel; wherein said first and second tumor cells or cell lines are of the same tissue type, but are distinct from one another (e.g., distinct in morphology, growth rate, and/or at least one mutation (e.g., a tumor-inducing mutation)); and (d) non-cancerous (i.e., normal or differentiated) tissue cells in said hydrogel, wherein said non-cancerous cells are of the same tissue type as said first and second cell type. One or more of the cells in the artificial cell construct may comprise and/or be labeled with a detectable compound. In some embodiments, one or more of the different populations and/or types of cells in the artificial cell construct may be distinguished from each other by a detectable signal (e.g., an optical and/or electrical signal that may be provided by a detectable compound).

An additional aspect of the present invention is directed to a method of preparing an artificial cell construct, the method including encapsulating an organoid in a crosslinked hydrogel, thereby preparing the artificial cell construct. In some embodiments, the method may include seeding the organoid on a hydrogel that is at least partially crosslinked; adding a hydrogel composition over the organoid; and crosslinking the hydrogel composition and/or the hydrogel to provide the crosslinked hydrogel.

A further aspect of the present invention is directed to a method of using a cell construct of the present invention, the method may include administering a compound to the cell construct; and detecting a physiological, pharmacological, and/or toxicological response to the compound.

Another aspect of the present invention is directed to a method of screening a test compound and/or of monitoring cell and/or tumor behavior. The method may comprise providing an organoid of the present invention; contacting a test compound to the organoid; and determining behavior (e.g., growth, metastasis, etc.) and/or amount of cells (e.g., tumor and/or non-cancerous tissue cells) in the organoid after contact with the test compound.

A further aspect of the present invention is directed to a method of determining a treatment and/or treatment regimen for a subject, the method comprising: providing an organoid of the present invention; contacting a test compound to the organoid; and determining behavior (e.g., growth, metastasis, etc.) and/or amount of cells (e.g., tumor cells and/or non-cancerous tissue cells) in the organoid, thereby determining a treatment and/or treatment regimen for the subject. In some embodiments, the organoid is provided and/or prepared by obtaining a tissue sample (e.g., a tumor biopsy) comprising tumor cells from the subject; separating different populations of cells in the tissue sample to provide one or more separate populations of cells with at least one, two, three, four or five of the one or more separate populations of cells comprising tumor cells; labeling at least one of the one or more separate populations of cells with a detectable compound (e.g., a fluorescent tag) to provide one or more labeled populations of cells with each of the one or more labeled populations of cells having a different detectable signal; and/or providing and/or combining the one or more labeled populations of cells in a hydrogel.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF ILLUSTRATIVE EMBODIMENTS

Figure 1:
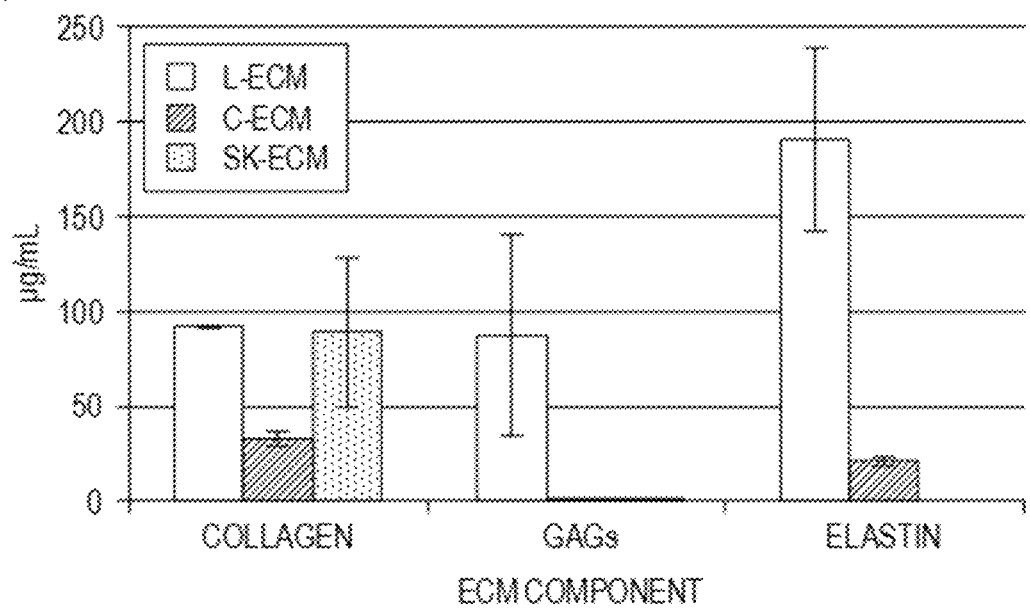
FIG. 1. Analysis of components present in tissue ECM-derived solutions for providing biochemical factors to hydrogel bioinks. A) A panel displaying the growth factors and cytokines amounts (pg/ml) measured in liver, cardiac, and skeletal muscle ECM solutions. B) The concentrations of collagen, GAGs, and elastin in liver, cardiac, and skeletal muscle ECM solutions.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof. As used herein, the term "and/or" includes any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The term "about," as used herein when referring to a measurable value such as an amount or concentration and the like, is meant to encompass variations of ±20%, ±10%, ±5%, ±1%, ±0.5%, or even 0.1% of the specified value as well as the specified value. For example, "about X" where X is the measurable value, is meant to include X as well as variations of ±20%, ±10%, ±5%, ±1%, ±0.5%, or even ±0.1% of X. A range provided herein for a measureable value may include any other range and/or individual value therein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

The cell constructs and/or organoids of the present invention are artificial in that the cell constructs and/or organoids are created or engineered in vitro. While one or more cells may be obtained or derived from a subject to prepare a cell construct and/or organoid of the present invention, the cell construct and/or organoid is prepared from discrete, individual cells outside the subject and is not a natural structure, construct, and/or tissue obtained from a subject.

"Organoid" is used interchangeably with "three-dimensional tissue construct" herein, and refers to a composition of live cells, typically in a carrier media, arranged in a three-dimensional or multi-layered configuration (as opposed to a monolayer). An organoid is an artificial, three-dimensional construct created in vitro to mimic or resemble the functionality and/or histological structure of an organ or a portion thereof. Suitable carrier media include hydrogels, such as, e.g., those described herein (e.g., cross-linked hydrogels), growth media, etc. Organoids may comprise one cell type or two or more (e.g., 2, 3, 4, 5, 6, or more) cell types, depending upon the particular tissue or organ being modeled or emulated. Some organoids may comprise cancer cells, as discussed further below. When organoids comprise cancer cells, they may include tissue cells, and/or may include a tissue mimic without cells, such as an extracellular matrix (or proteins or polymers derived therefrom), hyaluronic acid, gelatin, collagen, alginate, etc., including combinations thereof. In some embodiments, one or more types of cells that may be the same and/or different are mixed together with a hydrogel (e.g., an extracellular matrix or cross-linked matrix) to form an organoid or construct. In some embodiments, cell aggregates such as spheroids or organoids, optionally comprising one or more types of the cells that may be the same and/or different, may be pre-formed and then combined with a hydrogel (e.g., an extracellular matrix). In some embodiments, an organoid of the present invention may express a biomarker in the same amount or in an amount that is ±20%, ±10%, or ±5% of the average amount produced and/or expressed by corresponding cells in vivo.

In some embodiments, an organoid of the present invention is about 50, 100, or 200 µm to about 250 or 350 µm in diameter, such as, for example, about 50, 100, 150, 200, 250, 300, or 350 µm. The organoid may comprise about 1,500 or 2,000 to about 3,000, 3,500, 5,000, or 10,000 cells in total.

"Growth media" as used herein may be any natural or artificial growth media (typically an aqueous liquid) that sustains the cells used in carrying out the present invention. Examples include, but are not limited to, an essential media or minimal essential media (MEM), or variations thereof such as Eagle's minimal essential medium (EMEM) and Dulbecco's modified Eagle medium (DMEM), as well as high glucose media, blood, blood serum, blood plasma, lymph fluid, etc., including synthetic mimics thereof. In some embodiments, the growth media includes a pH color indicator (e.g., phenol red). In some embodiments, the growth media is a high glucose media.

"Test compound" or "candidate compound" as used herein may be any compound (e.g., a chemical and/or biological compound) for which a pharmacological and/or physiological activity, on a cell and/or tissue, or an interaction between two test compounds, is to be determined. In some embodiments, a test compound may be used to determine if the test compound has immunological activity, which may include testing for immunoglobulin generation, chemokine generation and/or cytokine generation by the cells, and/or activity in inhibiting the proliferation and/or spreading of cancer cells. For demonstrative purposes, Defactinib is used below as a test compound. However, any compound may be used, typically organic compounds such as proteins, peptides, nucleic acids, and/or small organic compounds (aliphatic, aromatic, and mixed aliphatic/aromatic compounds) may be used. In some embodiments, a test compound may be a WNT modulator and/or a chemotherapeutic. Candidate compounds may be generated by any suitable techniques, including randomly generated by combinatorial techniques, and/or rationally designed based on particular targets. See, e.g., A. M. Stock et al., Targets for anti-metastatic drug development, Curr. Pharm. Des. 19(28): 5127-34 (2013).

"Detectable compound" as used herein may be a fluorescent compound (e.g., a fluorescent protein (e.g., red fluorescent protein, green fluorescent protein, etc.)), an antigenic protein or peptide to which an antibody coupled to an enzyme, fluorescent, or radioactive group, or other label, will specifically bind, or any other suitable detectable compound. The detectable compound may be one naturally occurring in a cell (e.g., a cancer cell, such as, e.g., a cell marker protein that is expressed at higher levels in cancer cells than non-cancer cells), or one inserted into a cell by genetic engineering/recombinant DNA techniques (i.e., heterologous). In some embodiments, the detectable compound is a quantum dot (QD), a fluorescent organic dye, and/or a fluorescent protein.

A detectable compound may be any suitable compound that provides and/or generates a detectable signal that allows for differentiation and/or identification of a cell and/or cell population. A detectable signal may be provided and/or generated by one or more detectable compounds associated with a cell. In some embodiments, the detectable signal is a signal (e.g., an optical and/or electrical signal) that is generated by one or more detectable compounds (e.g., chemicals, proteins, etc.) associated with (e.g., applied to, attached to, bound to, compounded with, etc.) a cell. A detectable signal may be optically and/or electronically detectable, which may be perceived visually with the human eye and/or electronically read, detected, and/or obtained using methods known to those of skill in the art. In some embodiments, a detectable signal for a cell and/or cell population may be the absence of a signal (i.e., no detectable signal such as, e.g., no detectable fluorescence from the cell). In some embodiments, a detectable signal for a cell and/or cell population is a fluorescence signal.

A device and/or system of the present invention may comprise a detector (e.g., a camera) and/or an excitation source (e.g., an excitation light source). The detector may detect and/or image the detectable signal from a cell and/or cell population. The excitation source may be used to and/or may generate the detectable signal, such as, e.g., may be used to provide and/or generate light which may cause a detectable compound to fluoresce and thereby provide and/or generate the detectable signal.

In some embodiments, at least a portion of a device (e.g., a microfluidic device) of the present invention is transparent. For example, in some embodiments, the top and/or bottom substrate of the device may be transparent and/or the hydrogel present in the device may be transparent. The device may comprise a detector (e.g., a camera) operatively associated with the device. The detector may be operatively associated with one or more of the chambers of the device. In some embodiments, the detector is provided above and/or below the device and an excitation source may be provided above and/or below the device. In some embodiments, the detector comprises the excitation source (e.g., the light such as the flash and/or LED of a camera). The detector may be configured for detecting (e.g., imaging) cells in one or more chambers of the device. In some embodiments, the device may include a detector (e.g., a LED/CCD detector) positioned to allow images of labeled cells in contact with one or more chambers of the device to be imaged and/or quantified in real time. In some embodiments, the detector may capture images (e.g., fluorescent images) at predetermined intervals and/or may capture images and/or incidences of colonization, migration, and/or growth of labeled cells in and/or from an organoid present in the one or more chambers, which may enable real-time observation and/or quantitation of cells in the organoid and/or their growth, metastasis, migration, and/or the like.

A composition of the present invention may be used to prepare a cell and/or tissue construct of the present invention. Compositions of the present invention may comprise live cells in a "bioink," where the "bioink" is in turn comprised of a cross-linkable prepolymer, a post-deposition crosslinking group or agent; and other optional ingredients, including but not limited to growth factors, initiators (e.g., of cross-linking), water (to balance), etc. The compositions may be in the form of a hydrogel. In some embodiments, a composition of the present invention is a bioink that does not comprise cells. Various components and properties of the compositions are discussed further below.

Any type of cells, generally live cells, may be used to carry out the present invention, including but not limited to plant, animal, and microbial cells (e.g., yeast, bacteria, etc.). The cells may be combinations of multiple cell types, including combinations of cells from the same organism or species, symbiotic combinations of cells of different species, etc. In some embodiments, the cells are animal cells (e.g., bird, reptile, amphibian, etc.) and in some embodiments are mammalian cells (e.g., dog, cat, mouse, rat, monkey, ape, human). The cells may be differentiated or undifferentiated cells, but are, in some embodiments, tissue cells (e.g., brain cells, liver cells such as hepatocytes, pancreatic cells, cardiac muscle cells, skeletal muscle cells, etc.). Where tissue cells are employed, they may be incorporated as one cell type of multiple cell types for that tissue, and may be incorporated as discrete cells, or as cell aggregates such as organoids (which organoids may be unencapsulated or encapsulated; e.g., spheroids). In some embodiments, a cell present in an organoid may be labeled with, associated with, and/or may comprise a detectable compound such as, e.g., a fluorescent and/or radioactive compound. In some embodiments, an organoid of the present invention comprises two or more (e.g., 2, 3, 4, 5, 6, 7, or more) different types of cells (e.g., two or more different types of brain cells) providing two or more different populations of cells and each of the populations of cells are labeled with, associated with, and/or comprise a different detectable compound (e.g., a different fluorescent compound) so that each population of cells can be identified and/or distinguished (e.g., optically and/or electrically).

In some embodiments, cells may be obtained from a subject, such as, for example, a subject or patient undergoing treatment for cancer and/or that has cancer. Biopsy-derived cells (e.g., tumor and/or benign) may be used to form and/or prepare an organoid of the present invention, and the resulting organoid may be prepared and/or used in a method and/or device of the present invention within about 1, 2, 3, 4, 5, 6, 7, or 8 days after the biopsy. In some embodiments, the cells (e.g., tumor and/or benign) may be labeled with, associated with, and/or comprise a detectable compound, such as, but not limited to, a fluorescent compound (e.g., dye, protein, etc.).

In some embodiments, the cells are tumor cells, such as, e.g., patient biopsy-derived tumor cells, and organoids prepared from such cells may be used to screen potentially effective drugs and/or treatments. The cells may be differentiated at least in part to a particular cell or tissue type, such as brain, liver, intestine, pancreas, lymph node, smooth muscle, skeletal muscle, central nerve, peripheral nerve, skin, immune system, etc. Some cells may be cancer cells, as discussed further below, in which case they may express (naturally, or by recombinant techniques) a detectable compound.

In some embodiments, an organoid of the present invention is not prepared from and/or does not comprise cells from an immortalized cell line. Organoids of the present invention may comprise and/or be prepared using high functioning cells, such as, but not limited to, primary cells and/or stem cells, e.g., induced pluripotent stems and/or differentiated iPS-derived cells.

Choice of cells will depend upon the particular organoid being created and/or the organ and/or tissue desired to be modeled. For example, for a liver organoid, liver hepatocyte cells may be used. For a brain tumor organoid, brain tumor cells (e.g., glioblastoma cells) and/or non-cancerous brain tissue cells (e.g., astrocytes) may be used. The differentiated cells may be differentiated upon initial incorporation into the composition, or undifferentiated cells that are subsequently differentiated may be used. Cells collected from a patient may be de-differentiated and re-differentiated as needed.

Cancer cells used in the present invention may be any type of cancer cell, such as solid tumor cells including, but not limited to, melanoma, carcinoma, sarcoma, blastoma, glioma, and astrocytoma cells, etc. In some embodiments, a cell construct and/or organoid of the present invention comprises one or more (e.g., 1, 2, 3, 4, 5, 6, or more) glioblastoma cells or cell lines, such as, but not limited to, U87, U87 (ΔEGFR), U138, U373, and/or A172 cell lines and/or one or more cells or cell lines (e.g., 1, 2, 3, 4, 5, 6, or more) representative of the Proneural, Neural, Classical, and/or Mesenchymal glioblastoma subtype. In some embodiments, the one or more glioblastoma cells and/or brain cells may be obtained from a subject (e.g., from a tumor biopsy from the subject). In some embodiments, a cell construct and/or organoid of the present invention comprises at least one cell or cell line that is representative of each of the Proneural, Neural, Classical, and Mesenchymal glioblastoma subtypes (http://cancergenome.nih.gov/researchhighlights/researchbriefs/foursubtypes).

Where cancer cells and non-cancerous cells are present in a cell construct and/or organoid of the present invention, they may be present in any suitable ratio. In some embodiments, the cancer cells and non-cancerous cells may be present in a ratio similar to a ratio present in a subject. In some embodiments, the ratio of cancer cells to non-cancerous cells may be about 1:1 to about 20:1, such as, for example, about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, or any range or value therein. Alternatively, the ratio of non-cancerous cells to cancer cells may be about 1:1 to about 20:1, such as, for example, about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, or any range or value therein.

The cells may be incorporated into a composition of the present invention in any suitable form, including as unencapsulated cells, or as cells previously encapsulated in spheroids. Animal tissue cells encapsulated or contained in polymer spheroids can be produced in accordance with known techniques, or in some cases are commercially available (see, e.g., Insphero AG, 3D *Hepg2 Liver Microtissue Spheroids* (2012); Inspherio AG, 3D *InSight™ Human Liver Microtissues*, (2012)).

An organoid of the present invention may be in any suitable shape and/or form such as, e.g., any three-dimensional shape or multi-layered shape. In some embodiments, an organoid of the present invention may be in the form of a spheroid. An organoid of the present invention may be self-organized in a suspension or medium and optionally may be in the form of a spheroid. In some embodiments, the cells forming and/or present in the organoid may be suspended in a composition and/or bioink of the present invention. In some embodiments, an organoid of the present invention such as, e.g., a brain organoid, may comprise endothelial cells on one side of a semi-porous membrane and epithelial cells on the opposite side of the semi-porous membrane. Thus, the organoid may comprise a layer of endothelial cells and a layer of epithelial cells that are separated by a semi-porous membrane. The endothelial cells and epithelial cells may each be cultured on a surface (i.e., opposing surfaces) of the semi-porous membrane. The semi-porous membrane may be a silicon and/or polycarbonate-based membrane.

An organoid of the present invention may provide a patient-specific model system, which may be used to determine a treatment and/or treatment regimen for the patient (e.g., subject), optionally before initiation of therapy and/or treatment. In some embodiments, a test compound may be screened for anti-tumor activity, optionally in addition to an additional screening method, such as, but not limited to, genetic biomarker assessment and/or genetic profiling. In some embodiments, an organoid and/or method of the present invention may allow and/or provide for cellular biomarker recognition, biomarker expression quantification, and/or real time testing of chemotherapy drug efficacy.

Any suitable prepolymer can be used to carry out the present invention, so long as it can be further cross-linked to increase the elastic modulus thereof after deposition when employed in the methods described herein.

In some embodiments, the prepolymer is formed from the at least partial crosslinking reaction of: (i) an oligosaccharide (e.g., hyaluronic acid, collagen, combinations thereof, and particularly thiol-substituted derivatives thereof) and (ii) a first crosslinking agent (e.g., a thiol-reactive crosslinking agent, such as polyalkylene glycol diacrylate, polyalkylene glycol methacrylate, etc., and particularly polyethylene glycol diacrylate, etc.; thiolated crosslinking agent to create thiol-thiol disulfide bonds; gold nanoparticles, and/or gold functionalized crosslinkers forming thiol-gold bonds; etc., including combinations thereof).

In some embodiments, the compositions include a post-deposition crosslinking group. Any suitable crosslinking groups can be used, including but not limited to multi-arm thiol-reactive crosslinking agent, such as polyethylene glycol dialkyne, other alkyne-functionalized groups; acrylate-functionalized groups (e.g., polyethylene glycol functionalized with one or more acrylate groups), etc., including combinations thereof.

Compositions of the invention may optionally, but in some embodiments preferably, include an initiator (e.g., a thermal or photoinitiator). Any suitable initiator that catalyzes the reaction between said prepolymer and the second (or post-deposition) crosslinking group (e.g., upon heating or upon exposure to light), may be employed.

A composition of the present invention may optionally, but in some embodiments preferably, include at least one growth factor (e.g., appropriate for the particular cells included, and/or for the particular tissue substitute being produced). An example is a decellularized extracellular matrix composition ("ECM") from a tissue corresponding to the tissue cells of the construct (e.g., decellularized extracellular liver matrix when the live animal cells are liver cells; decellularized extracellular cardiac muscle matrix when the live animal cells are cardiac muscle cells; decellularized skeletal muscle matrix when the live animal cells are skeletal muscle cells; decellularized extracellular brain matrix when the live animal cells are brain cells; etc.). Additional collagens, glycosaminoglycans, and/or elastin (e.g., which may be added to supplement the extracellular matrix composition), etc., may also be included.

A composition of the present invention may have an elastic modulus, at room temperature and atmospheric pressure, sufficiently low such that it can be manipulated and deposited on a substrate by whatever deposition method is employed (e.g., extrusion deposition). Further, the composition optionally, but in some embodiments preferably, has an elastic modulus, again at room temperature and atmospheric pressure, sufficiently high so that it will substantially retain the shape or configuration in which it is deposited until subsequent cross-linking (whether that cross-linking be spontaneous, thermal or photo-initiated, etc.). In some embodiments, the composition (e.g., the bioink), prior to deposition, has a stiffness of from about 0.05, 0.1 or 0.5 to about 1, 2, 5 or 10 kiloPascals, or more, at room temperature and atmospheric pressure. After deposition and/or crosslinking, the stiffness of the composition may increase and/or the composition may gel. In some embodiments, the composition is in the form of a hydrogel after deposition and/or crosslinking and has a stiffness of from about 0.05, 0.1, 0.5, 1, or 5 to about 10, 20 or 50 kiloPascals at room temperature and atmospheric pressure. In some embodiments, the composition is in the form of a hydrogel after deposition and/or crosslinking and has a stiffness of about 0.05, 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 kiloPascals or any range therein.

In some embodiments, a composition of the present invention is a bioink that is in the form of a hydrogel and does not comprise cells. The hydrogel may be a non-natural hydrogel in that the hydrogel structure or network does not exist naturally in a subject even though one or more components of the hydrogel may be present in a subject. For example, the hydrogel structure or network may comprise a crosslinked polymer and such a crosslinked polymer structure is not naturally present in a subject. The hydrogel may be a hyaluronic acid based hydrogel. In some embodiments, the hydrogel comprises thiol modified hyaluronan, an acrylate functionalized polyethylene glycol (e.g., thiol reactive polyethylene diacrylate (PEGDA) and/or PEG-4 ARM crosslinker), thiol modified gelatin (i.e., denatured collagen), and/or heparin. A hydrogel of the present invention may mimic one or more aspects or properties of a tumor environment (e.g., the stiffness of the tumor environment), such as, for example, a brain tumor environment. In some embodiments, the stiffness of a hydrogel of the present invention may be controlled and/or modulated to study the effect of stiffness (e.g., matrix stiffness) on cells (e.g., tumor cells).

In some embodiments, a hydrogel of the present invention may comprise hyaluronic acid in an amount of about 0.1% w/v to about 2% w/v, gelatin in an amount of about 0.1% w/v to about 4%, and one or more crosslinkers in an amount of about 0.1% w/v to about 10% w/v, and optionally prior to deposition the hydrogel may not comprise cells. In some embodiments, hyaluronic acid is present in a hydrogel of the present invention in an amount of about 0.1%, 0.25%, 0.5%, 0.75%, 1%, 1.25%, 1.5%, 1.75%, or 2% w/v, or any range and/or individual value therein. In some embodiments, a hydrogel of the present invention comprises one or more (or the total amount of) crosslinker(s) in an amount of about 0.1%, 0.25%, 0.5%, 0.75%, 1%, 2%, 3%, 4%, 5%, 6%, 7%, 8%, 9%, or 10% w/v or any range and/or individual value therein. In some embodiments, gelatin is present in a hydrogel of the present invention in an amount of about 0.1%, 0.25%, 0.5%, 0.75%, 1%, 1.5%, 2%, 2.5%, 3%, 3.5%, or 4% w/v, or any range and/or individual value therein.

In some embodiments, the stiffness of a hydrogel of the present invention (in the presence or absence of cells) can be controlled and/or tuned. The stiffness of the hydrogel may be increased or decreased by modifying (e.g., increasing or decreasing) the amount of crosslinking group present in the hydrogel, by the type of crosslinking group present in the hydrogel (e.g., PEGDA vs. PEG-4 ARM), and/or by the length of time the hydrogel may be crosslinked. In some embodiments, the stiffness of the hydrogel may be decreased by adding collagenase and/or hyaluronidase to the hydrogel. In some embodiments, the stiffness of the hydrogel may be increased or decreased by modifying (e.g., increasing or decreasing) the amount of hyaluronic acid and/or gelatin in the hydrogel. In some embodiments, the stiffness of the hydrogel may be modified by including a crosslinker with a breakable bond such as, e.g., a disulfide bond. For example, the stiffness of a hydrogel may be decreased by using a degradable PEGDA like crosslinker that contains a breakable bond such as a disulfide bond (PEG-SS-DA) rather than using PEGDA. The breakable bond may be broken by a thiophilic molecule such as, e.g., N-acetyl-L-cysteine and/or glutathione, and thus may reduce the overall stiffness of the hydrogel.

The compositions of the invention may be used in any convenient manner. According to some embodiments of the present invention provided are methods of making a tissue construct in a device of the present invention. In one non-limiting method, a composition of the present invention is used in a method of making a three-dimensional construct. Such a method may comprise the steps of:
  (a) providing a reservoir containing an extrudable hydrogel composition as described above, then
  (b) depositing the hydrogel composition onto a substrate (e.g., by extrusion through a syringe); and then
  (c) cross-linking said prepolymer with said second cross-linking group by an amount sufficient to increase the stiffness of said hydrogel and form said three-dimensional construct (e.g., by heating the hydrogel, irradiating the hydrogel composition with light (e.g., ambient light, UV light), altering the pH of the hydrogel; etc.).

The depositing step may be carried out with any suitable apparatus, including but not limited to that described in H.-W. Kang, S. J. Lee, A. Atala and J. J. Yoo, US Patent Application Pub. No. US 2012/0089238 (Apr. 12, 2012). In some embodiments, the depositing step is a patterned depositing step, that is, deposition is carried out so that the deposited composition is deposited in the form of a regular or irregular pattern, such as a regular or irregular lattice, grid, spiral, etc.

In some embodiments, the cross-linking step increases the stiffness of said hydrogel by from 1 or 5 to 10, 20 or 50 kiloPascals, or more, at room temperature and atmospheric pressure.

In some embodiments, the hydrogel has a stiffness after said cross-linking step (c) of from 1 or 5 to 10, 20 or 50 kiloPascals at room temperature and atmospheric pressure.

In some embodiments, the method further comprises the step of depositing a supporting polymer (e.g., poly-L-lactic acid, poly(glycolic acid), polycaprolactone; polystyrene; polyethylene glycol, etc., including copolymers thereof such as poly(lactic-co-glycolic acid)) on said substrate in a position adjacent that of said hydrogel composition (e.g., concurrently with, after, or in alternating repetitions with, the step of depositing said hydrogel, and in some embodiments prior to the cross-linking step).

Any suitable substrate can be used for the deposition, including organic and inorganic substrates, and including substrates with or without features such as well, chambers, or channels formed thereon. For the particular products described below, the substrate may comprise a microfluidic device having at least one chamber (e.g., 1, 2, 3, 4, 5, 6, 7, 8, or more chambers) (the at least one chamber optionally but preferably associated with an inlet channel and/or an outlet channel), and the depositing is carried out in at least one chamber. In an alternative, the substrate may comprise a first planar member (e.g., a microscope cover slip), the depositing step may be carried out that planar member, and the method may further comprise the step of inserting that planar member into a chamber of a microfluidic device. Post-processing steps, such as sealing of chambers, and maintaining the viability of cells, may be carried out in accordance with known techniques.

An organoid and/or cell construct of the present invention may more closely resemble and/or replicate the environment of a natural tissue and/or tumor in a subject (e.g., the brain tumor microenvironment in a subject) compared to an animal model, 2D cell culture, and/or a tissue construct prepared in the absence of a method of the present invention.

According to some embodiments, a method of preparing a cellular model is provided. The method may comprise seeding a plurality of cells on a hydrogel of the present invention. The plurality of cells may be seeded on the hydrogel so that the cells have no contact with a substrate (e.g., a well plate) on which the hydrogel is in contact with and/or placed. Cell culture media may be added over and/or to cover the plurality of cells seeded on the hydrogel. The plurality of cells may comprise cancer cells, optionally two or more different types of cancer cells. The cellular model may be referred to as a 2½ D model and may be used to study the effect of matrix stiffness on individual cells. The results from such a study may be applied to understand the effect of single migratory cells, such as, for example, brain cancer cells. The method may further comprise administering at least one test compound to the cellular model (e.g., by adding the test compound to the growth medium in contact with the cellular model) and detecting a pharmacological and/or toxicological response to the test compound in a cell present in the cellular model.

In some embodiments, a method of preparing a cell construct is provided and may comprise encapsulating an organoid (e.g., a spheroid) in a hydrogel of the present invention. Some embodiments include seeding an organoid on a hydrogel of the present invention that optionally has been at least partially crosslinked; adding a composition of the present invention (e.g., a bioink) onto the organoid on the hydrogel to form a combined hydrogel composition; and crosslinking the composition and/or hydrogel (e.g., by exposing the composition and/or hydrogel to UV light), thereby encapsulating the organoid in the combined hydrogel composition. In some embodiments, the hydrogel may be crosslinked at least partially (or entirely) prior seeding the organoid onto the hydrogel. The composition added onto the organoid on the hydrogel may be the same as or different than the hydrogel. In some embodiments, the only difference between the hydrogel and composition is that the hydrogel is at least partially crosslinked prior to being seeded with the organoid and the composition is not crosslinked prior to being added over the organoid. In some embodiments, the method may comprise adding or contacting a growth media to the encapsulated organoid and/or the combined hydrogel composition. The method may further comprise administering at least one test compound to the encapsulated organoid (e.g., by adding the test compound to the growth media) and detecting a pharmacological or toxicological response to the test compound in the organoid.

An organoid, cell construct, and/or cell used in a method and/or system of the present invention may comprise any type of cell as described above. In some embodiments, an organoid, cell construct, and/or plurality of cells may comprise two or more (e.g., 2, 3, 4, 5, 6, 7, or more) different types of cells, which may be from the same organism or species (e.g., from the same subject, such as, e.g., a subject with cancer). The two or more different types of cells may be two types of cells from multiple cell types for a particular tissue. For example, an organoid and/or cell construct may two or more types of brain cells, liver cells, endothelial cells, or immune cells that may be different or distinct in morphology, growth rate and/or at least one mutation (e.g., at least one tumor-inducing mutation). In some embodiments, the organoid, cell construct, and/or plurality of cells may comprise cancer cells, optionally two or more (e.g., 2, 3, 4, 5, 6, 7, or more) different types of cancer cells. For example, an organoid and/or cell construct may comprise at least five different primary cancer cells or cell lines, and one or more of the at least five different primary cancer cell lines may comprise at least one different mutation than another of the at least five primary cancer cell lines. In some embodiments, an organoid and/or cell construct of the present invention achieves intra tumor heterogeneity that is similar to that observed in vivo in a subject (e.g., a subject with cancer or being treated for cancer). In some embodiments, an organoid and/or cell construct of the present invention may comprise one or more (e.g., 1, 2, 3, 4, 5, 6, 7, or more) types of non-cancerous tissue cells and/or one or more (e.g., 1, 2, 3, 4, 5, 6, 7, or more) tumor cells or cell line types. The one or more non-cancerous tissue cells and/or the one or more tumor cells or cell line types may be the same tissue type and/or a different tissue type. In some embodiments, an organoid may comprise one or more non-cancerous tissue cells such as, e.g., neurons, astrocytes, glial cells, and/or endothelial cells, and may comprise one or more tumor cells such as, e.g., tumor cells having different mutations and/or surface markers, and the non-cancerous tissue cells and/or tumor cells may be the same tissue type and/or may be from a subject, optionally from a tumor biopsy from the subject. In some embodiments, the organoid and/or cell construct may comprise at least one cell type that is a different tissue type than the tumor cell or cell line and/or non-cancerous tissue cells. When two or more tumor cells or cell line types are included in an organoid and/or cell construct, the cell lines may have one or more different mutations between them to provide a heterogenous cell construct. In some embodiments, a cell or cell line may comprise one or more oncogenes and/or tumor suppressor genes listed in the tables at https://www.cancerquest.org/cancer-biology/cancer-genes#table.

An organoid and/or cell construct of the present invention may comprise astrocytes and one or more GBM cells or cell line types selected from the group consisting of U87, U87 (ΔEGFR), U138, U373, and/or A172. These GBM cell line types may have one or more mutations as listed in Table 1.

TABLE 1

Example mutations in GBM cell lines

| Cell line | Mutations |
| --- | --- |
| A172 | CDKN2A, PTEN and EGFR (190 Kda mutation) |
| U87 | CDKN2A, NF1 and PTEN |
| U138 | P53* and EGFR upregulation |
| U373 | P53* and EGFR upregulation |
| U87 (ΔEGFR) | EGFR VIII (2-7 Deletion mutation) |

In some embodiments, the tumor cell line may be a glioblastoma cell line, which may contain a mutation in the TP53 gene, IDH1 gene, IDH2 gene, PDGFRA gene, NF1 tumor suppressor gene, and/or PTEN gene. In some embodiments, the tumor cell comprises a mutation in the TP53 gene, IDH1 gene, IDH2 gene, PDGFRA gene, NF1 tumor suppressor gene, and/or PTEN gene. The organoid and/or cell construct may be classified as one or more of the following GBM subtypes: Proneural, Neural, Classical, and/or Mesenchymal. In some embodiments, the GBM organoid and/or cell construct may comprise at least one cell type that is a different tissue type than the GBM cell or cell line and/or non-cancerous brain tissue cells, such as, for example, vascular endothelial cells and/or immune cells.

According to some embodiments of the present invention, provided is a method of studying the effects of matrix and/or hydrogel stiffness on cells (e.g., tumor cells). The method may comprise using a cellular model and/or cell construct of the present invention. Two or more cellular models and/or cell constructs may be used with each of the two or more cellular models and/or cell constructs comprising a hydrogel with a different stiffness than another. One or more physiological, pharmacological, and/or toxicological responses of the cells and/or organoids in the respective cellular model or cell construct may be measured and/or compared to determine the effects of matrix and/or hydrogel stiffness on cells.

In some embodiments provided are methods of modulating the stiffness of a tumor microenvironment and/or cell construct, the method may comprise administering collagenase, hyaluronidase, and/or a compound that targets breakable bonds within the hydrogel to the tumor and/or artificial cell construct. In some embodiments, the stiffness of the environment in which a cell construct is present may be modulated and the cells of the cell construct may be from a subject with cancer. In some embodiments, the method comprises before and/or after the administering step, determining and/or measuring the amount of cellular proliferation, cell viability, cellular migration, and/or cellular invasion and/or determining and/or measuring the stiffness modulus of the environment (e.g., the hydrogel). In some embodiments, a method of the present invention may modulate (e.g., increase or decrease) the stiffness of a cell environment (e.g., a tumor cell environment), which may modulate (e.g., decrease) the proliferation and/or migration of a cell (e.g., tumor cell) in the cell environment. Modulating the cell environment may delay disease and/or tumor progression and/or may prevent or reduce the invasion of cancer cells in to normal tissues.

According to some embodiments of the present invention, provided is a personalized cancer model, which may be used for drug and/or toxicology studies. Cells (e.g., non-cancerous and/or tumor cells (e.g., brain tumor cells)) from a subject (e.g., a subject or patient being treated for cancer and/or that has cancer) may be used in and/or used to prepare a cellular model, cell construct, and/or organoid of the present invention. Embodiments of the present invention, optionally used in combination with Magnetic Resonance Electrography (MRE) to determine stiffness and/or elastic modulus in the brain and/or a tumor in a subject, may be used to predict mutations in GBM in a subject before biopsy is performed on and/or done in a subject and/or to determine and/or administer a treatment regimen in the subject. In some embodiments, a method of the present invention may use MRE to measure brain tissue stiffness, for example, to demarcate the tumor from normal tissue, which optionally may not otherwise be differentiated. In some embodiments, MRE and/or MRE data may be used to manage and/or monitor tumor pseudo progression and/or pseudo response (e.g. in glioblastoma).

A variety of different products may be made with the methods and compositions described above. In a non-limiting, but preferred, example, the product may be a device useful for modeling animal tissue function (such as liver or brain function) in vitro. Such a device may comprise: (a) a device body such as a microfluidic device having at least one chamber formed therein; (b) a hydrogel composition deposited in said chamber in a first pattern, (c) live animal tissue cells in said hydrogel composition; and (d) a structural support polymer deposited in said chamber adjacent said hydrogel. As noted above, the cells for such a device may comprise animal tissue cells, such as liver cells (e.g., hepatocytes), pancreatic cells, brain cells, skeletal muscle cells; cardiac muscle cells, etc.

The device body or microfluidic device may itself be formed of any suitable material or combination of materials. Examples include, but are not limited to, polydimethylsiloxane (PDMS), polystyrene, polymethyl methacrylate (PMMA), polyacrylamide, polyethylene glycol (PEG) including functionalized PEG (e.g. PEG diacrylate, PEG diacrylamide, PEG dimethacrylate, etc., or any of the foregoing PEGs in in multi-arm forms, etc.), natural polymers or proteins that can be cross-linked or cured (e.g., hyaluronic acid, gelatin, chondroitin sulfate, alginate, etc., including derivatives thereof that are functionalized with chemical groups to support cross linking, and including any of the "cross-linkable prepolymers" described above in crosslinked form, and combinations thereof. The device body may be formed by any suitable process, including molding, casting, additive manufacturing (3d printing), lithography, etc., including combinations thereof.

Where a structural support is included in the device, that structural support, like the hydrogel, may be patterned (e.g., a regular or irregular pattern, such as a regular or irregular lattice, grid, spiral, etc.).

In some embodiments, the tissue cells are contained in spheroids (e.g., polymer spheroids), which spheroids are contained in said hydrogel.

As noted above, the hydrogel is preferably cross-linked following deposition, such that the hydrogel residing in the device has a stiffness of from 1 or 5 to 10, 20 or 50 kiloPascals at room temperature and atmospheric pressure. In some embodiments, the hydrogel has a stiffness corresponding to the natural tissue and/or tumor in which the cells are found in vivo.

The device may be provided as a cartridge, or as a subcombination unit or "building block" configured in a manner suitable for "snap in" installation in a larger apparatus including pumps, detectors, or the like, as discussed further below.

Once produced, subcombination or "cartridge" devices as described above may be used immediately, or prepared for storage and/or transport.

To store and transport the product, a transient protective support media that is a flowable liquid at room temperature (e.g., 25° C.), but gels or solidifies at refrigerated temperatures (e.g., 4° C.), such as a gelatin mixed with water, is added into the device to substantially or completely fill the chamber(s), and preferably also any associated conduits. Any inlet and outlet ports are capped with a suitable capping element (e.g., a plug) or capping material (e.g., wax). The device is then packaged together with a cooling element (e.g., ice, dry ice, a thermoelectric chiller, etc.) and all placed in a (preferably insulated) package.

Alternatively, to store and transport the product, a transient protective support media that is a flowable liquid at cooled temperature (e.g., 4° C.), but gels or solidifies at warmed temperatures such as room temperature (e.g., 20° C.) or body temperature (e.g., 37° C.), such as poly(N-isopropylacrylamide and poly(ethylene glycol) block co-polymers.

Upon receipt, the end user simply removes the device from the associated package and cooling element, allows the temperature to rise or fall (depending on the choice of transient protective support media), uncaps any ports, and removes the transient protective support media with a syringe (e.g., by flushing with growth media).

A device of the present invention may be configured to provide a physiological or hyperphysiological fluid to tissue volume ratio. For example, one or more chambers in the device may have an average volume in a range of about 2 μL to about 10 μL. In some embodiments, one or more chambers in the device may have an average volume of about 2, 3, 4, 5, 6, 7, 8, 9, or 10 μL. In some embodiments, a device of the present invention (e.g., a device comprising at least 2 or 6 chambers) may use liquid in the amount of and/or have a volume of less than about 100 μL, such as, e.g., about 95, 90, 85, 80, 75, 70, 65, 60, 55, 50, 45, 40 μL or less. The volume of the device, as used herein, refers to the volume to fill the chamber(s) and channel(s) of the device. In some embodiments, a device of the present invention (e.g., a device comprising at least 2 or 6 chambers) may use liquid in the amount of and/or have a volume of less than about 50 µL. In some embodiments, the volume of the device may be increased by integration and/or use with an external fluid reservoir. The external fluid reservoir may increase the overall system volume and/or aid in controlling the volume of the device.

A system, device, and/or method of the present invention may comprise and/or provide one or more (e.g., 1, 2, 3, 4, 5, 6, 7, 8, or more) different tissues and/or organoids (e.g., 3D organoids) that each are viable for at least 1, 2, 3, 4, or more weeks. In some embodiments, a system, device, and/or method of the present invention comprises and/or provides one or more (e.g., 1, 2, 3, 4, 5, 6, 7, 8, or more) different organoids that are in fluid communication with each other and a common aqueous growth media, and that are each viable for at least 1, 2, 3, 4, or more weeks. Thus, in some embodiments, two, three, four, five, six, or more different organoids are in fluid communication with each other and a common aqueous growth media, and each is viable for at least 1, 2, 3, 4, or more weeks. In some embodiments, one or more of the organoids may be viable and may comprise at least about 75% or more (e.g., about 80%, 85%, 90%, 95% or more) living cells based on the average number of cells present in the construct at 1, 2, 3, 4, or more weeks. The tissues and/or organoids may be generated by differentiation from a common cell sample (e.g., a sample such as a skin sample collected from a subject). One or more of the organoids may comprise cells in proportions similar to the proportions of cells present in the corresponding native (e.g., human) tissue. In some embodiments, at least one of the organoids comprises metastatic and/or malignant cells. In some embodiments, a function and/or property of the tissue and/or organoid may be determined and/or measured and compared to the function and/or property of a corresponding native tissue (e.g., a property of a brain organoid may be measured and compared to the same property of a brain tissue in a subject). In some embodiments, a function and/or property of the tissue and/or organoid may be similar to the function and/or property of a corresponding native tissue.

According to some embodiments of the present invention provided are methods of using an organoid of the present invention. In some embodiments, a method of screening a test compound and/or a method of monitoring cell and/or tumor behavior is provided. In some embodiments, a method of evaluating tumor cells in vitro (e.g., useful for evaluating metastasis of tumor cells in vitro, for evaluating tumor cell migration and/or invasion in vitro, for evaluating growth of a construct comprising tumor cells in vitro, and/or for evaluating response to a test compound of interest, such as, e.g., a drug) is provided. A method of the present invention may comprise providing an organoid of the present invention, contacting at least one test compound to the organoid, and determining behavior (e.g., growth, metastasis, etc.) and/or amount of cells (e.g., tumor cells) in the organoid after contact with the at least one test compound. In some embodiments, a method of the present invention may monitor and/or determine population shift and/or changes (e.g., clonal evolution) over time, optionally in real-time. A method of the present invention may comprise and/or utilize a step and/or device as described in PCT/US17/45277, the contents of which are incorporated by reference herein.

In some embodiments, an organoid used in a method of the present invention may comprise at least two tumor cells or cell lines that are of the same tissue type, but are distinct from one another (e.g., distinct in morphology, growth rate, and/or at least one mutation) and at least one type of non-cancerous (i.e., normal or differentiated) tissue cell, wherein the at least one type of non-cancerous tissue cell is of the same tissue type as the at least two tumor cells or cell lines, and wherein the at least two tumor cells or cell lines and the at least one type of non-cancerous cell can be distinguished (e.g., visually and/or optically distinguished) from each other. In some embodiments, at least one of the cells in the organoid (e.g., the non-cancerous cells) are not labeled with a detectable compound. In some embodiments, one or more of the different types and/or populations of cells (e.g., tumor cells) or cell lines are labeled with, associated with, and/or comprise a detectable compound.

In some embodiments, an organoid of the present invention comprises a core comprised of live tumor cells and optionally non-cancerous tissue cells (e.g., astrocytes), the core may be surrounded (e.g., encapsulated) by a hydrogel, the hydrogel optionally comprising one or more non-cancerous tissue cells (e.g., neurons, astrocytes, glial cells, endothelial cells, etc.). Thus, in some embodiments, an organoid of the present invention may comprise a core and a shell surrounding the core, the shell comprising non-cancerous tissue cells. In some embodiments, the shell and/or hydrogel has a stiffness that mimics and/or is substantially the same as tissue in vivo (e.g., brain extracellular matrix stiffness).

In some embodiments, an organoid used in a method of the present invention is prepared from cells obtained from a subject, such as, e.g., from a tissue sample and/or tumor biopsy from a subject. An organoid of the present invention may be prepared by obtaining a tissue sample (e.g., a tumor biopsy) from a subject; separating different populations of cells in the tissue sample to provide one or more separate populations of cells; labeling one or more of the one or more separate populations of cells with a detectable compound (e.g., a fluorescent tag) to provide one or more labeled populations of cells with each of the one or more labeled populations of cells having a different detectable signal; and/or combining the one or more labeled populations of cells to form the organoid. The tissue sample (e.g., tumor biopsy) may be genetically sequenced in part or in full in order to identify mutations, and any mutations identified may indicate and/or suggest one or more compound(s) of interest for therapeutic purposes for the subject (e.g., anti-tumor activity). The method may comprise screening the one or more compound(s) of interest that were identified in the genetic sequencing and contacting each of the one or more compound(s) of interest and/or a combination thereof to the organoid prepared using the cells from the tissue sample. An organoid of the present invention may have the same or substantially the same heterogeneity as a tumor found in vivo in a subject.

In some embodiments, separating the different populations of cells in the tissue sample may comprise separating the cells by subtype (e.g., by GBM subtype surface marker) into one or more different sub-clones, thereby providing the one or more separate populations of cells. Methods of separating different populations of cells are known to those of skill in the art and any suitable method may be used, such as, but not limited to, fluorescence activated cell sorting (FACS).

The one or more labeled populations of cells may be combined in any suitable manner. In some embodiments, the one or more labeled populations of cells may be added to the same common media and/or hydrogel. In some embodiments, the one or more labeled populations of cells may be used to form an organoid as described herein that is encapsulated by a hydrogel of the present invention. One or more different populations of cells in an organoid of the present invention may be present in substantially the same (e.g., within about ±20%) amount as the amount of cells in that population in a tissue and/or tumor in vivo. In some embodiments, when cells have been obtained from a tissue sample from subject, sorted and/or labeled, the different populations of cells are combined in substantially the amount as the amount present in the tissue sample.

A test compound may be contacted to an organoid in any suitable manner. In some embodiments, the test compound is added to growth media that is in contact with the organoid (e.g., circulated to the organoid).

Determining behavior and/or amount of cells (e.g., tumor cells) in an organoid may be done at any point in time, optionally at any point in time after contact with a test compound. In some embodiments, determining behavior and/or amount of cells in the organoid may be done in real-time and/or at 1, 2, 3, 4, 5, 6, 7, 8, 9 or more different points in time, optionally after contact with 1, 2, 3, or more test compounds. In some embodiments, the behavior and/or amount of cells may be compared over time. In some embodiments, the behavior and/or amount of cells is determined about 1, 2, 3, 4, 5, 6, 7, or more days and/or weeks after contact with a test compound.

In some embodiments, determining behavior and/or amount of cells in an organoid after contact with a test compound comprises determining a decrease in metastasis of the tumor cells in the organoid, a decrease in organoid size, a decrease in the number of tumor cells and/or non-cancerous tissue cells in the organoid, and/or tumor and/or non-cancerous tissue cell death in the organoid, optionally as compared to metastasis, organoid size, number of tumor cells and/or non-cancerous tissue cells, and/or tumor and/or non-cancerous tissue cell death in a control organoid (i.e., a like organoid) that is not contacted with the test compound. The control organoid may be an additional organoid prepared from the same collection of cells and/or tissue sample and/or is provided and/or encapsulated in the same hydrogel (e.g., a hydrogel having the same composition).

In some embodiments, determining behavior and/or amount of cells (e.g., tumor and/or non-cancerous tissue cells) in the organoid after contact with a test compound comprises comparing to the behavior of the cells and/or the amount of cells in the organoid prior to contact with the test compound. For example, the amount of tumor cells and/or the non-cancerous tissue cells before and after administration of a test compound may be compared. In some embodiments, the amount of tumor cells and/or the non-cancerous tissue cells in each of the one or more labeled populations before and after administration of a test compound is compared.

The growth of tumor cells and/or non-cancerous tissue cells may be determined in a method of the present invention. In some embodiments, growth of tumor cells and/or the non-cancerous tissue cells in an organoid that is contacted with a test compound may be compared to the growth of tumor cells and/or non-cancerous tissue cells in a control organoid. In some embodiments, a decrease in growth of the tumor cells (e.g., lack of proliferation of the tumor cells, death of the tumor cells, decrease in invasion of the tumor cells, etc.) may indicate anti-tumor activity of the test compound.

In some embodiments, a method of the present invention comprises determining the genetic profile of an organoid of the present invention, optionally before, during, and/or after contacting with a test compound. The genetic profile of the organoid before contact with the test compound may be compared to the genetic profile of the organoid after contact with the test compound (e.g., about 1, 2, 3, 4, 5, 6, 7 or more days and/or weeks after contact with the test compound). In some embodiments, determining the genetic profile of the organoid comprises determining the genotype and/or phenotype of one or more cells in the organoid. In some embodiments, GBM subtype heterogeneity (genotype and phenotype) in the organoid is determined.

As described herein, one or more test compounds may be contacted to an organoid of the present invention, optionally at one or more different points in time (e.g., at about 1, 2, 3, 4, 5, 6, 7, 8, 9, 10 or more hours, days, and/or weeks after a prior test compound). In some embodiments, a method of the present invention comprises contacting a second test compound to an organoid after a first test compound has been contacted. Behavior (e.g., growth, metastasis, etc.) and/or the amount of tumor cells and/or the non-cancerous tissue cells in the organoid after contact with the second test compound may then be determined (e.g., 1, 2, 3, 4, 5, 6, 7, or more days and/or weeks after contact with the second test compound). In some embodiments, a method of the present invention may determine one or more cell populations that are contributing to tumor reoccurrence and/or migration, optionally after a first treatment and/or contact of an organoid with a first test compound. In some embodiments, a method of the present invention may comprise determining a second treatment for a subject based on which cell population may be growing, increasing in number and/or migrating after contact with a first test compound and/or treatment. In some embodiments, a method and/or system of the present invention may provide and/or monitor one or more cell populations that may be found in a tumor in a subject, and may allow for one or more drugs and/or treatments to be investigated in vitro to determine effectiveness for the subject. In some embodiments, a method and/or system of the present invention reproduces and/or monitors one or more changes in tumor heterogeneity in vitro, optionally in real-time and optionally with one or more cell populations from a tumor from a subject.

Provided according to some embodiments is a method of determining a treatment and/or treatment regimen for a subject. In some embodiments, the method may comprise providing an organoid of the present invention, contacting a test compound to the organoid, and determining behavior (e.g., growth, metastasis, etc.) and/or amount of cells (e.g, tumor cells and/or non-cancerous tissue cells) in the organoid, thereby determining a treatment and/or treatment regimen for the subject. In some embodiments, the organoid is prepared and/or obtained by obtaining a tissue sample (e.g., a tumor biopsy) comprising tumor cells from the subject; separating different populations of cells in the tissue sample to provide one or more separate populations of cells with at least one, two, three, four or five of the one or more separate populations of cells comprising tumor cells; labeling at least one of the one or more separate populations of cells with a detectable compound (e.g., a fluorescent tag) to provide one or more labeled populations of cells with each of the one or more labeled populations of cells having a different detectable signal; and/or combining the one or more labeled populations of cells, optionally in a hydrogel, to form an organoid.

A method of the present invention may comprise administering a test compound to a subject (e.g., a subject from which cells were obtained to prepare an organoid of the present invention), optionally in a treatment-effective amount, when the test compound is determined to decrease the metastasis of the tumor cells in the organoid, decrease organoid size, decrease the number of tumor cells in the organoid, and/or provide tumor cell death in the organoid, optionally as compared to metastasis, organoid size, number of tumor cells, and/or tumor cell death in a control organoid that is not contacted with the test compound.

In some embodiments, a method and/or organoid of the present invention may provide and/or allow for results (e.g., drug screening results and/or therapeutic analysis) within about 1 or 2 weeks (e.g., within about 2, 3, 4, 5, 6, 7, 8, 9, or 10 days) after a biopsy (e.g., a tumor biopsy) from a subject is obtained, the cells of which were used to prepare an organoid of the present invention that was used in a method and/or device as described herein.

The present invention is explained in greater detail in the following non-limiting Examples.

EXAMPLES

Example 1

Materials and Methods

Materials. Hydrochloric acid (HCl) was from Fischer Scientific (Houston, TX). Pepsin (porcine gastic mucosa) was from Sigma Aldrich (St. Louis, MO, USA). Heprasil (est. 160 kDa MW), Gelin-S, and Extralink (PEGDA, 3.4 kDa MW) were used from HyStem-HP hydrogel kits from ESI-BIO (Alameda, California, USA). PEG 4-Arm Acrylate (10 and 20 kDa MW), PEG 4-Arm Alkyne (10 kDa MW), and PEG 8-Arm Alkyne (10 kDa MW) were from Creative PEGWorks (Winston-Salem, North Carolina, USA).

Preparation of tissue-specific extracellular matrix (ECM) digest. Tissue-specific ECM digest solutions were prepared as previously described for liver (A. Skardal, L. Smith, S. Bharadwaj, A. Atala, S. Soker and Y. Zhang, *Biomaterials*, 33, 4565 (2012).). Fresh liver, cardiac, or skeletal muscle tissue was rinsed with chilled Dulbecco's phosphate buffered saline (DPBS). The tissues were cut into 10 cm by 0.5-1.0 cm strips and minced with surgical scalpels. Minced tissue was transferred to 500 ml distilled water and shook on a rotary shaker at 200 rpm for 3 days at 4° C., during which the water was changed three times per day. The tissues were treated with 2% Triton X-100 for 4 days followed by 2% TX-100 with 0.1% NH4OH for 24 h. During the TX-100 rinses, solutions were changed twice daily. The decellularized tissues were washed for 2 additional days in distilled water to remove any traces of TX-100, after which they were stored at 4° C. until further use.

Decellularized tissue ECMs were frozen and lyophilized for 48 h. Following lyophilization, samples were ground into a powder with a freezer mill. One gram of liver tissue or liver ECM powder was mixed with 100 mg Pepsin (Porcine gastric mucosa, 3400 units of protein, Fisher Scientific, Fair Lawn, NJ) and sterilized by gamma irradiation (1 Mrad). All subsequent procedures following sterilization were carried out under sterile conditions. Hydrochloric acid (0.1 N, 100 mL) was added to the sterilized materials and incubated for 48 h at room temperature. The resulting mixture was transferred to a 50 ml conical tube and centrifuged at 3000 rpm for 15 min. The supernatant was removed and the pellet was discarded. This was repeated 3 times until the supernatant was clear. To ensure there was no more particulate matter remaining, the suspension was filtered through a 0.45 mm syringe filter (Fisher Scientific). The resulting decellularized ECM solutions were stored at 80° C. until further use.

Hydrogel bioink formulations and preparation. Prior to hydrogel formulation, a photonitiator, Irgacure 2959 (4-(2-hydroxyethoxy)phenyl-(2-propyl)ketone, Sigma), was dissolved in water at 0.05% w/v. To form hydrogel bioinks, first the base material components from HyStem-HP hydrogel kits (ESI-BIO, Alameda, CA) were dissolved in the water-phoinitiator solution. Briefly, Heprasil and Gelin-S were dissolved in water-phoinitiator solution to make 2% w/v solutions. Extralink, the crosslinker, was dissolved in water-phoinitiator solution to make a 4% and 8% w/v solution. Additionally, multi-arm PEG-based crosslinkers were prepared separately: PEG 4-Arm Acrylate (10 kDa or 20 kDa MW; 4% and 8% w/v), PEG 4-Arm Alkyne (10 kDa MW; 4% w/v), and PEG 8-Arm Alkyne (10 kDa MW; 8%, 10%, 16% and 20% w/v).

Following dissolution of all materials, hydrogels were formulated by 2 general schemes. In the first, 4 parts 2% Heprasil, 4 parts 2% Gelin-S, 1 part crosslinker 1, 1 part crosslinker 2 is combined with 10 parts tissue ECM solution (or water as a generic non-tissue-specific hydrogel). The resulting mixture is vortexed to mix prior to use. For extrusion or bioprinting testing, the mixture is transferred into a syringe or printer cartridge and allowed to crosslink spontaneously for 30 minutes (stage 1 crosslinking). For rheological measurements, the mixture is transferred into a 35 mm petri dish and allowed to crosslink. In the second formulation approach, the Heprasil, Gelin-S, and crosslinker solution is not further diluted with tissue ECM solution or water in order to achieve an increased polymer concentration. Instead, the photoinitiator is dissolved in the tissue ECM solutions at 0.05% w/v, which subsequently is used to dissolve the Heprasil, Gelin-S, and various crosslinkers. These components are then combined in the same 4:4:1:1 volume ratio. The materials were transferred into syringes, printer cartridges or petri dishes and allowed to spontaneously crosslink (stage 1 crosslinking) as described above for implementation. For secondary crosslinking (stage 2) the stage 1-crosslinked gels are irradiated with ultraviolet light (365 nm, 18 w/cm$^2$) to initiate a thiol-alkyne polymerization reaction.

Printer compatibility testing. Extrusion-based bioprinting was tested first on the laboratory bench with simple extrusion tests using standard syringes and small gauge needle tips (20-30 gauge). Next, bioink preparations were loaded into printer cartridges, allowed to undergo spontaneous stage 1 crosslinking, and extrusion compatibility for bioprinting was assessed using a custom 3-D bioprinting device designed in house specifically for tissue construct printing (See, e.g., H. Kang, S. Lee, A. Atala and J. Yoo, US Patent Application Pub. No. US 2012/0089238 (Apr. 12, 2012)). A 7×7 mm pattern was implemented for testing purposes. To improve shear thinning and extrusion properties, unmodified HA and gelatin was supplemented to the bioinks (1.5 mg/mL and 30 mg/mL) (Sigma). The tendency for the bioink to be extruded smoothly versus in irregular clumps was observed.

Determination of bioink mechanical properties by rheology. For determination of bioink mechanical properties, hydrogels were prepared as described above and pipetted into 35 mm petri dishes where they underwent the stage 1 spontaneous crosslinking. Rheological testing was performed using an HR-2 Discovery Rheometer (TA Instruments, Newcastle, DE). A 12-mm steel disc was lowered until contact with the surface of the hydrogel was made. The disc was lowered further until the axial force on the instrument, or normal force acting on the disc from the hydrogel, equaled 0.4 N. At this point G' was measured for each hydrogel using a shear stress sweep test ranging from 0.6 to 10 Pa at an oscillation frequency of 1 Hz applied by the rheometer.

For determination of the stiffness after completion of the second stage crosslinking, identical untested hydrogels were further crosslinked by UV photopolymerization after which G' measurement was performed as described.

Bioprinting of liver organoids for biological validation of bioinks. Primary liver hepatocyte-based spheroids were formed by hanging drop method. Spheroids were harvested and suspended within a liver-specific bioink formulation containing liver ECM materials, drawn into a syringe compatible with the bioprinting, and the bioink was allowed to spontaneously crosslink through thiol-acrylate bonding. After 30 minutes, the spheroid-containing bioink was bioprinted within a polycaprolactone support pattern on a plastic coverslip. Following bioink depostion, UV light was used to initiate the second crosslinking step, stabilizing the bioink further and raising the bioink stiffness to a value similar to native liver, thus comprising the larger liver organoid. As a control, a gelatin-based hydrogel previously used in the bioprinter was used to bioprint spheroids in parallel. Following printing, viability of the organoids was assessed using a LIVE/DEAD stain, after which the organoids were fixed in paraformaldehyde, and imaged with a Leica TCS LSI macro-confocal microscope to determine the relative amounts of viable (green fluorescent) and dead (red fluorescent) cells.

Functional analysis of liver organoids and toxic insult. Organoids were prepared as described above. Nine organoids were placed in microreactors for 14 day culture time courses, during which media aliquots would be sampled and reserved for functional analysis. Microreactors were polydimethylsiloxane (PDMS) devices with chambers for organoid placement, and channels through which cell culture media can be circulated from a reservoir using a microperistaltic pump. After sampling media aliquots on day 3 and day 6 for baseline functional metrics, 3 organoids continued in culture with normal media; 3 organoids were administered media containing 1 mM acetaminophen, and 3 organoids were administered 10 mM acetaminophen in media. Media aliquots were collected on days 10 and 14, after which urea and albumin secretion were quantified and viability was assessed by LIVE/DEAD imaging.

Toxic insult and clinical relevant intervention with N-acetyl-L-cysteine. Organoids were prepared again as described above and placed in microreactor devices for 14 days of culture. After sampling media aliquots on day 3 and day 6 for baseline functional metrics, 1 group of organoids continued in culture with normal media; another group of organoids was administered media containing 10 mM acetaminophen, and the third group of organoids was administered 10 mM acetaminophen plus 20 mM N-acetyl-L-cysteine (NAC) in media. Media aliquots were collected on day 10 and 14, after which urea and albumin secretion were quantified Results: Characterization.

ECM component analysis. Liver ECM solutions were analyzed previously by a series of colorimetric assays (A. Skardal et al., supra). Two formulations were analyzed: 1) LEE, decellularized liver prepared as described above; and LTE, fresh liver tissue that was prepared identically, with the exception that it was not decellularized. The results revealed a clear trend, in which LEE solutions contained greater concentrations of collagen, glycosaminoglycans (GAGs), and elastin (FIG. 1A). Specifically, the total collagen content of LEE, 91.33 mg/mL, was significantly greater than that of LTE, which was 4.17 mg/mL (p<0.001), the elastin content of LEE, 189.33 mg/mL, was significantly greater than that of LTE, which was 36.00 mg/mL (p<0.05) and the GAG content of LEE, 86.00 mg/mL, was greater than that of LTE, which was 40.67 mg/mL, but not significantly (p>0.05).

Cardiac and skeletal muscle ECM solutions (both decellularized preparations) were assessed in the same manner.

Growth factor analysis. Liver ECM solutions were analyzed previously by the Quantibody Growth Factor Array, which revealed that, in general, LEE contained higher concentrations of growth factors and cytokines (shown in pg/mL, FIG. 1B). Of particular interest was that brain-derived neurotrophic factor (BDNF), bFGF, bone morphogenetic protein 5 (BMP-5), FGF-4, insulin-like growth factor binding protein 2 (IGFBP-2), and TGF-b1 were relatively conserved between both LEE and LTE. However, LEE also contained BMP-7, EGF, FGF-7, growth hormone (GH), heparin-binding EGF-like growth factor (HB-EGF), HGF and neurotrophin 3 (NT-3), which were not observed or were negligible in LTE. On the other hand, BMP-4, and glial-derived neurotrophic factor (GDNF) were present in LTE, but not in LEE (A Skardal et al., supra). Cardiac and skeletal muscle ECM solutions (both decellularized preparations) were assessed in the same manner.

Figure 2:
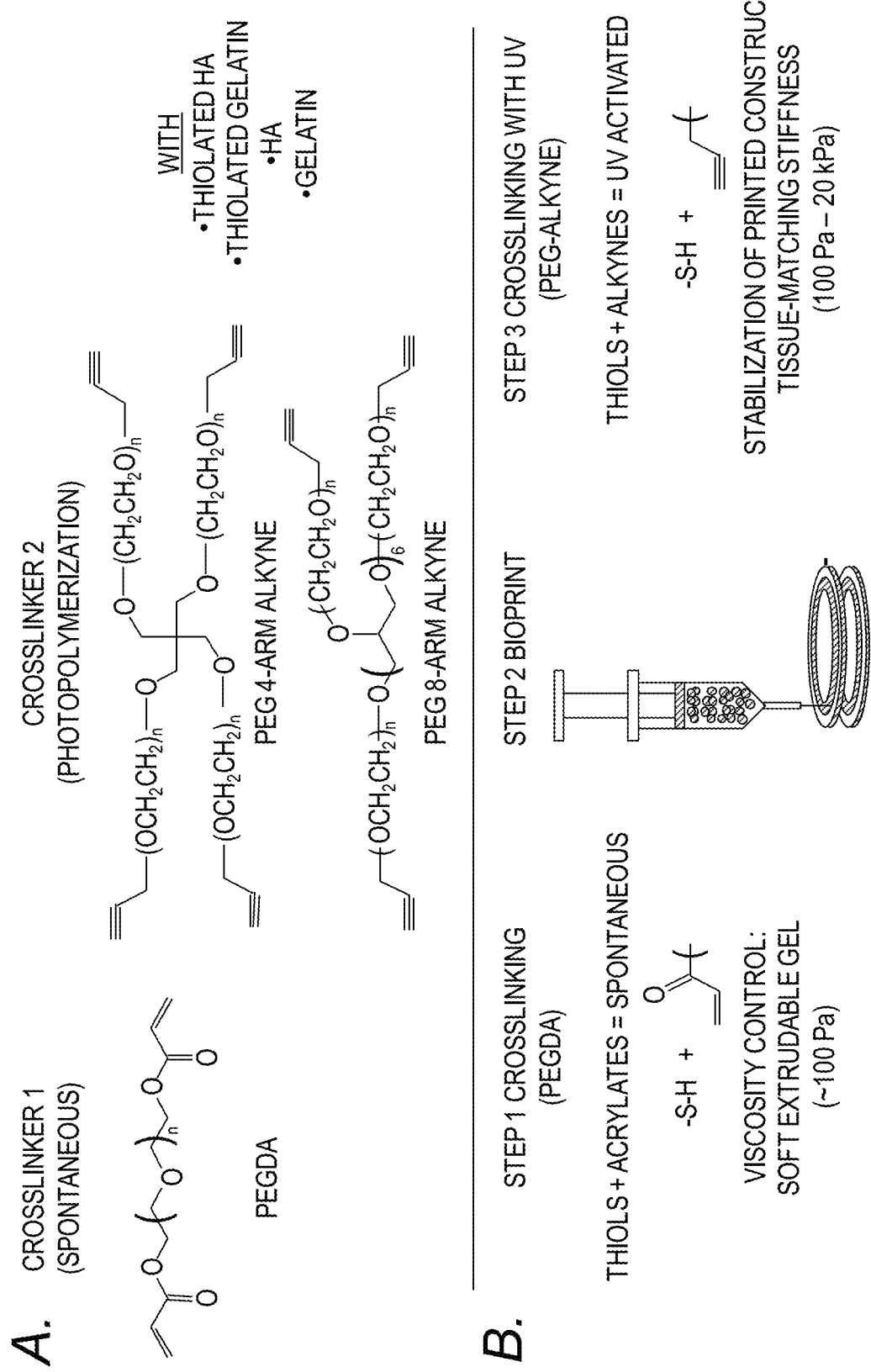
FIG. 2. A) Strategy of formulation of printable bioinks comprised of acrylate-based crosslinkers (crosslinker 1), alkyne-based crosslinkers (crosslinker 2), thiolated HA, thiolated gelatin, and unmodified HA and gelatin. B) Implementation of bioprintable hydrogel bioinks. The bioink formulation is prepared and spontaneously crosslinks through thiol-acrylate binding, resulting in a soft, extrudable material. Bioprinting is performed. Lastly, the bioprinted structures are fused, stabilized, and brought to the target stiffness.
Figure 3:
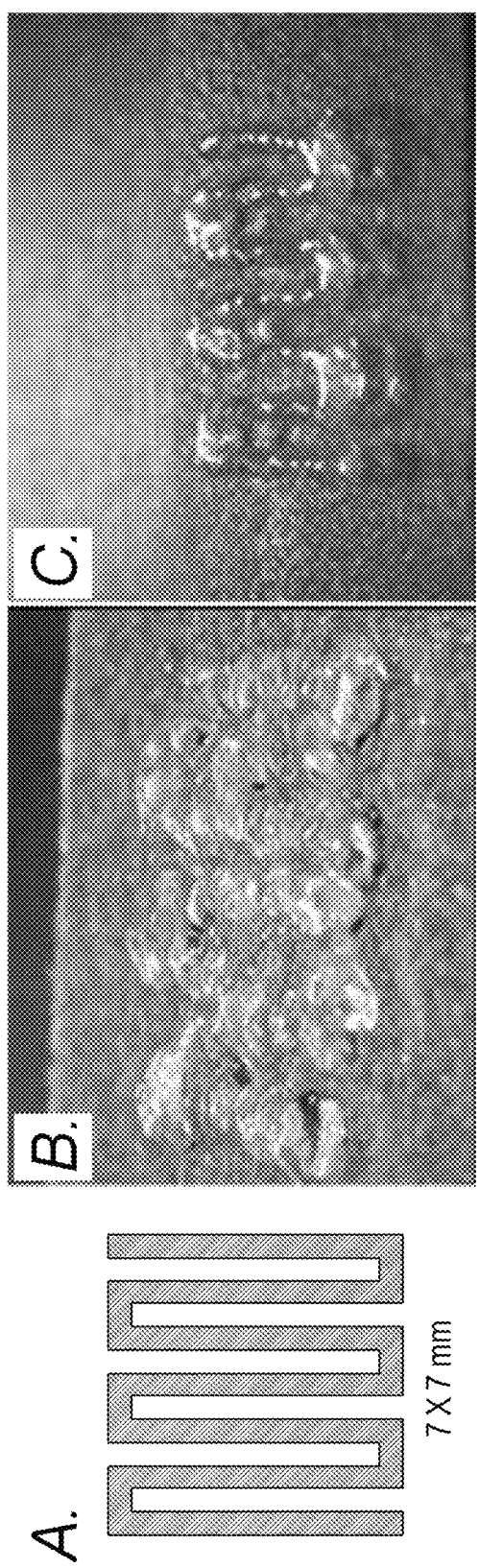
FIG. 3. Bioprinting testing of bioinks. A) A 7×7 mm pattern used for bioink deposition testing in the bioprinter. B) An initial formulation of a polyethylene diacrylate (PEGDA) and 4-arm PEG alkyne containing bioink after printing. C) Improved extrusion and end structure smoothness after addition of unmodified HA and gelatin to improve shear thinning and material smoothing.

Hydrogel bioink preparation and extrusion bioprinting testing. Strategy and implementation of stage 1 and stage 2 crosslinking of the hydrogel bioinks is described in FIGS. 2A and B. A 7×7 mm pattern was implemented for testing purposes (FIG. 3A). Initial tests showed that the initial formulations were extrudable, but appeared irregular and clumped during and after extrusion (FIG. 3B). To improve shear thinning and extrusion properties, unmodified HA and gelatin was supplemented to the bioinks (1.5 mg/mL and 30 mg/mL). The improved smooth printed structure is shown in FIG. 3C.

Figure 4:
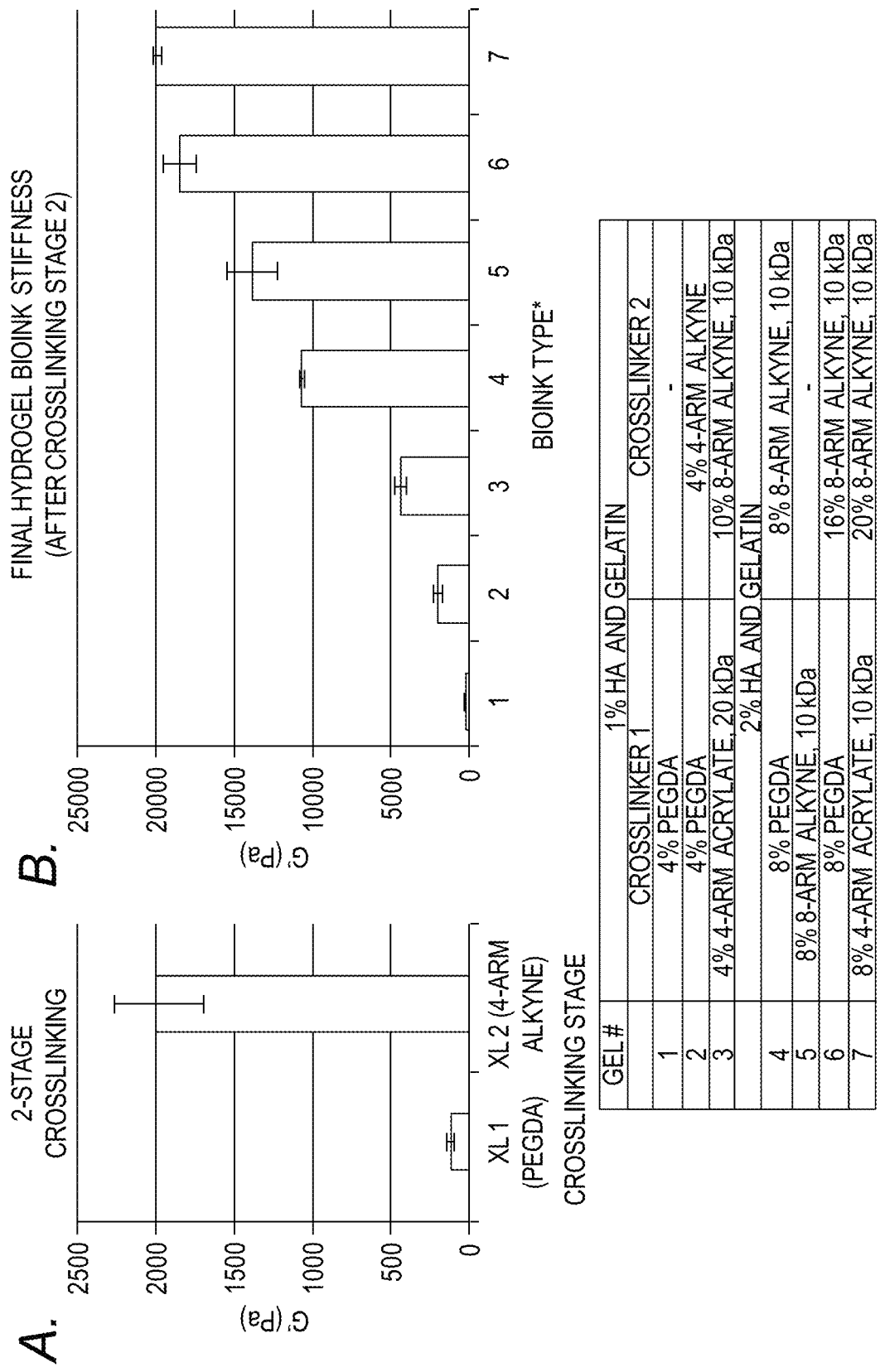
FIG. 4. Bioink stiffness control and range of formulations. A) Demonstration of the capability to control bioink stiffness using Gel #2 in this panel. After stage 1 crosslinking, the gel is relatively soft and able to be extruded smoothly. After stage 2 crosslinking by UV light, stiffness increases by more than an order of magnitude. B) A range of final stiffness levels of a variety of bioink formulations after stage 2 crosslinking, spanning from approximately 100 Pa to approximately 20 kPa.

Rheological testing. As described in the methods, hydrogels of different formulations were prepared for rheological assessment of their mechanical properties. FIG. 4A shows the increase in shear elastic modulus (G') in a gel that after spontaneous crosslinking with PEGDA had a G' of 113.66 Pa. This is the stage during which the hydrogel can be extruded as a bioink. After UV crosslinking with a 4-arm PEG Alkyne crosslinker, the G' value increases to 1981.79 Pa. FIG. 4B shows the range of G' values that can be achieved through the secondary Alkyne-based crosslinking step, allowing mimicry of many tissue types in the body. Table 1 shows a range of hydrogel stiffness within the range of this system, formulations, and associated tissue types.

TABLE 1

A) Formulations for creating liver, heart, and skeletal muscle-specific hydrogel biolinks.
B) Formulations for additional tissue types of interest.

|   | Tissue | Biochemical Parameters | Crosslinker 1 | Biofabrication G' | Crosslinker 2 | Endpoint G' |
|---|---|---|---|---|---|---|
|   |   |   |   | Physical Parameters | | |
| A | Liver | GFs/ECM from dissolve/decell liver tissue | PEGDA | 100-200 Pa | 8-Arm PEG Alkyne | ~10 kPa |

TABLE 1-continued

A) Formulations for creating liver, heart, and skeletal muscle-specific hydrogel biolinks.
B) Formulations for additional tissue types of interest.

| | | | | | |
|---|---|---|---|---|---|
| Heart | GFs/ECM from dissolve/decell cardiac tissue | PEGDA | 100-200 Pa | 8-Arm PEG Alkyne | ~10-15 kPa |
| Skeletal Muscle | GFs/ECM from dissolve/decell skeletal muscle tissue | 4-Arm PEG Acrylate | 200-400 Pa | 8-Arm PEG Alkyne | ~15-20 kPa |

| | Tissue | Biochemical Parameters | Physical Parameters | | | |
|---|---|---|---|---|---|---|
| | | | Crosslinker 1 | Biofabrication G' | Crosslinker 2 Endpoint G' | Target Endpoint G' |
| B | Bone Marrow | Bone marrow ECM | PEGDA | 100-200 Pa | PEG-Di-Alkyne/ 4-Arm PEG Alkyne Blend | ~1 kPa |
| | Fat | Fat ECM | PEGDA | 100-200 Pa | PEG-Di-Alkyne/ 4-Arm PEG Alkyne Blend | ~1 kPa |
| | Brain/Nerve | Brain/nervous tissue ECM | PEGDA | 100-200 Pa | 4-Arm PEG Alkyne | ~1-2 kPa |
| | Lung | Lung ECM | PEGDA | 100-200 Pa | 4-Arm APEG Alkyne | ~3-5 Kpa |
| | Kidney | Kidney ECM | PEGDA | 100-200 Pa | 8-Arm PEG Alkyne | ~10 kPa |
| | Smooth Muscle | Smooth muscle ECM | 4-Arm PEG Acrylate | 200-400 Pa | 8-Arm PEG Alkyne | ~10-15 kPa |
| | Cartilage/ Tendon | Cartilage/Tendon ECM | 4-Arm PEG Acrylate | 200-400 Pa | ? | 100-1000 kPa |

Results: Validation.

Figure 5:
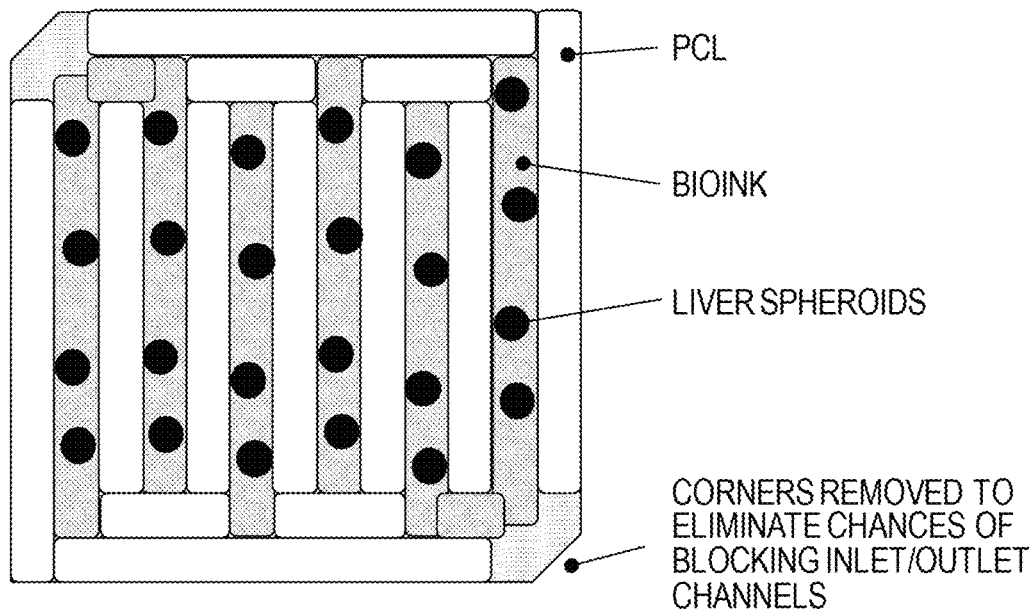
FIG. 5. Design of biofabricated organoids.

Bioink maintenance of primary organoid viability in a biofabrication bioprinting setting. The biofabricated organoids were designed as depicted in FIG. 5. Using the integrated printing approach of printing both polycaprolactone (PCL) and hydrogels, a PCL channel structure was printed inside of which the bioink with the liver cells was printed. The channel structures provide stability to the hydrogel when under flow as well as increasing the height-width aspect ratio of the hydrogel and cells. These structures were printed on plastic coverslips that were customized to fit inside the microfluidic microreactor chambers. These square coverslips feature 2 additional cuts in the corners to prevent occlusion of the micro-channels providing the inlet and outlet flows to the organoid chamber in the microreactors.

Most spherical organoids within the overall construct stayed spherical during the printing process and maintained their original shape in culture. In earlier batches without PCL channels, some organoids were observed to become disfigured, compressed, or even torn during the printing process. This indicates a substantial improvement in the biofabrication technique. Uniformity of spherical organoid distribution and quantity was improved. In this batch, each organoid construct that was moved to microreactor culture (n=9) contained between 40-45 spherical organoids. In past batches this number varied between 10 and 30.

Figure 6:
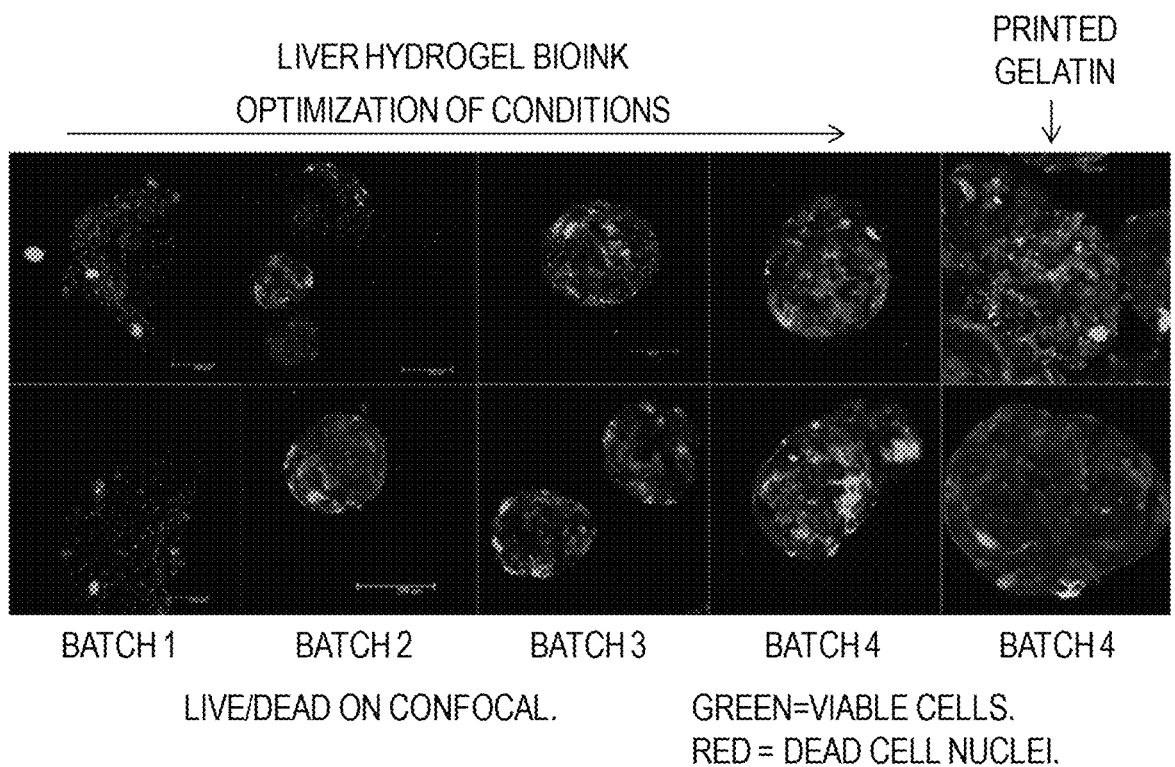
FIG. 6. LIVE/DEAD imaging of organoids after extrusion biofabrication in compositions of the invention.

Multiple batches of organoids were biofabricated allowing opimization of the biofabrication conditions. Temperature was adjusted to remain near 37° C. in the bioink and in the bioprinting chamber. Biofabrication preparation and methodology was performed in less time. Hepatocyte culture medium was added to the bioink to provide nutrients to the cells during printing. LIVE/DEAD imaging shows the increased viability of multiple iterations of the organoids after extrusion biofabrication in the bioink (FIG. 6). A gelatin control was used in parallel with Batch 4 as a comparison. Simple gelatin gels are commonly used for extrusion biofabrication.

Ability to support primary cell function in vitro using liver bioinks: Baseline secretory activity and toxic insult. Liver organoids were prepared and biofabricated as described above, placed in microfluidic microreactors and cultured for 14 days. On day 6, organoids received normal media, or 1 of 2 concentrations of APAP.

Figure 7:
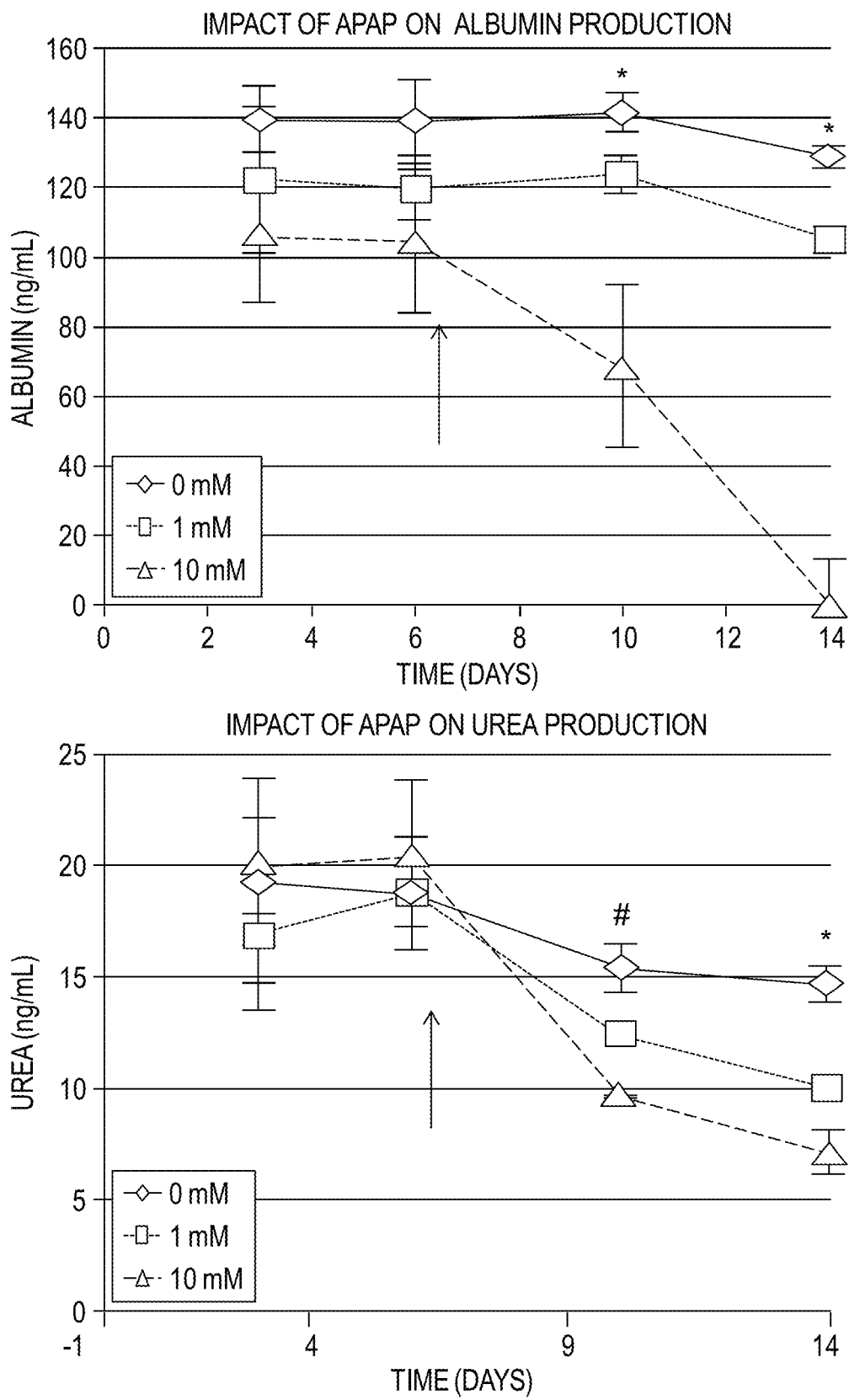
FIG. 7. Albumin and Urea analysis of organoids after extrusion biofabrication in compositions of the invention.

Albumin analysis (FIG. 7) by a Human Albumin ELISA Kit (Alpha Diagnostic International) revealed constant albumin production by bioprinted liver organoids through day 6, remaining on average near 120 ng/mL. It should be noted that during these 2 baseline timepoints we observed a trend in secretion magnitude, with 0 mM organoids secreting the most, followed by the 1 mM orgnanoid group, and then the 10 mM group. This decrease in baseline albumin production is believed to be due to the time at which the organoids were printed. The organoids in group 1 were printed first, and therefore have a slightly improved viability, which translates into improved albumin secretion. Despite this trend, albumin levels at these 2 time points were not statistically significant in comparison to one another. But in future studies, organoids will be randomly assigned to experimental treatment groups. Following APAP administration after day 6, albumin levels were significantly decreased in both the 1 mM and 10 mM groups compared to the 0 mM control ($p<0.05$). Additionally, the 10 mM group albumin levels were significantly decreased compared to the 1 mM group ($p<0.01$). In fact, at day 14 the albumin levels in the 10 mM group were nearly immeasurable.

Urea analysis (FIG. 7) by a QuantiChrom Urea Colorimetric Assay Kit (BioAssay Systems) showed less drastic results than the albumin analysis, yet the results were still significant statistically with expected trends. Urea levels were not significantly different between the 3 groups during the time points prior to APAP administration. After APAP administration, measured urea levels appeared to drop in a dose dependent manner with respect to APAP concentration. On the day 10 time point, the 0 mM control group albumin level was significantly higher than both the 1 mM and 10 mM group (p<0.05). On the day 14 time point, all 3 groups were significantly different from one another (p<0.05)

Figure 8:
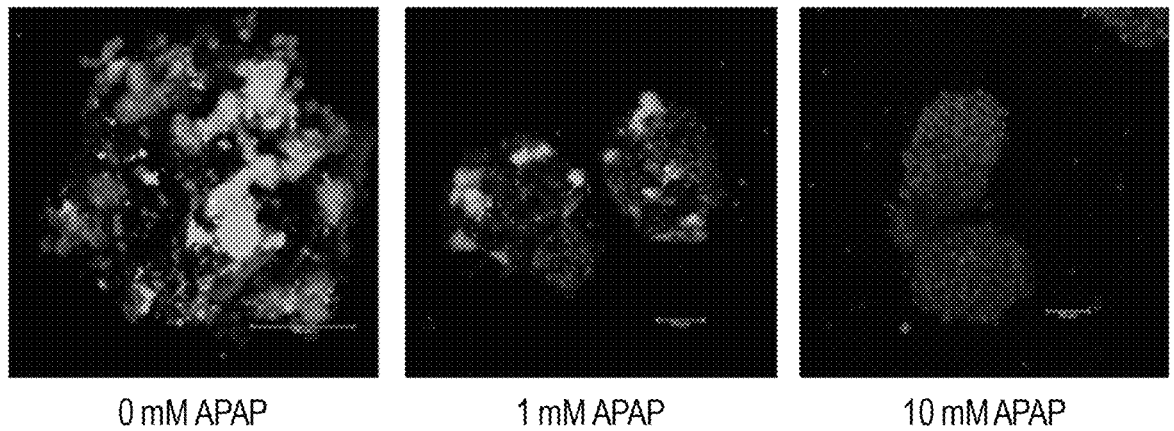
FIG. 8. Viability of acetaminophen (paracetamol; N-acetyl-p-aminophenol; "APAP") treated organoids assessed by LIVE/DEAD staining.

Viability of the 0 mM, 1 mM, and 10 mM APAP treated organoids was assessed by LIVE/DEAD staining and imaging using the macro-confocal microscope as has been described before (FIG. 8). Based on the ratio of live cells to dead cells, it was evident that the 0 mM control group maintained a relatively high level of viability (70-90% at day 14) throughout the 14 day experiment. In comparison, the 1 mM group had decreased viability (30-50% at day 14), while the 0 mM group appeared to have nearly no viable cells at day 14.

APAP toxicity testing and N-acetyl-L-cysteine intervention. As described previously, liver organoids will be prepared and bioprinted as described in previous reports. These organoids were used to set baseline functional metrics by media aliquots reserved on day 3 and day 6. Organoids would then undergo toxic insult by acetaminophen (10 mM), but some groups would also be administered N-acetyl-L-cysteine (20 mM) as a clinically relevant countermeasure. Media aliquots were reserved for functional analysis on days 3, 6, 10, and 14.

Figure 9:
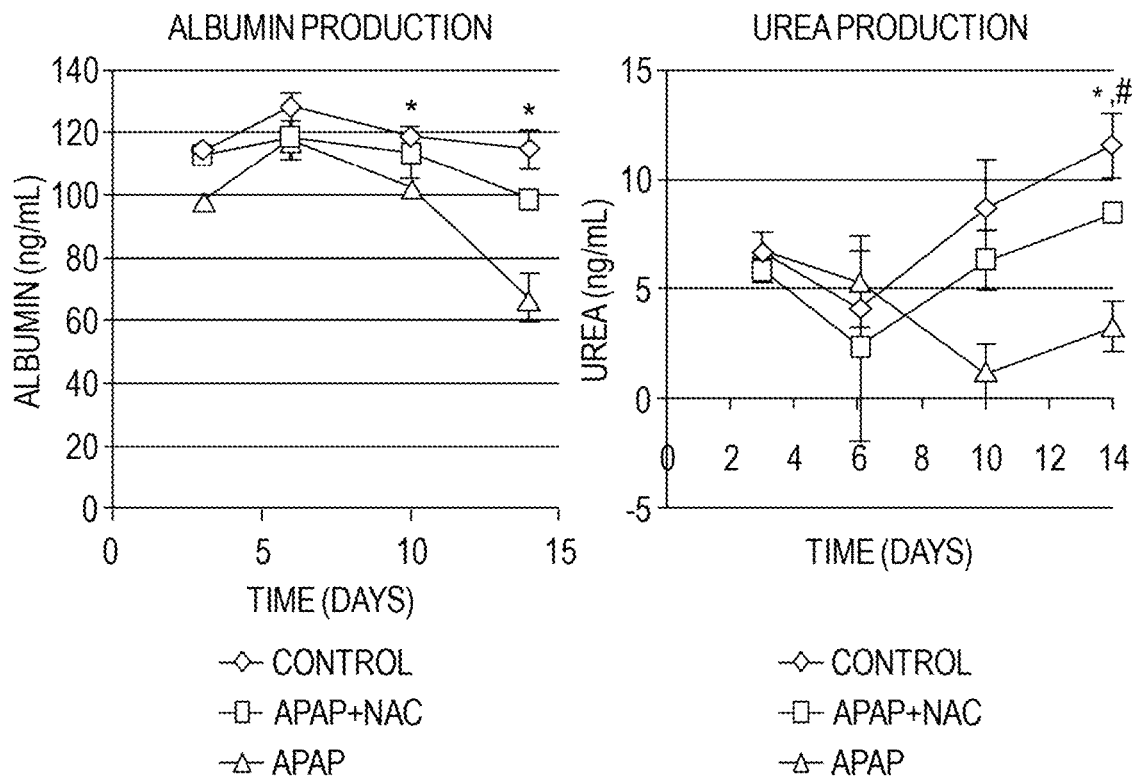
FIG. 9. Albumin and Urea analysis of organoids after APAP treatment.

Albumin analysis (FIG. 9) by a Human Albumin ELISA Kit (Alpha Diagnostic International) revealed constant albumin production by bioprinted liver organoids through day 6, remaining on average near 120 ng/mL, consistent with the experiment reported previously. Following administration of APAP only, we observed a decrease in detected albumin. This decrease was statistically significant (p<0.5) compared to the untreated control organoids at day 10 and day 15. The co-administration of APAP and NAC saw a slight decrease in detected albumin production, decreasing to 98 ng/mL by day 14, however, this value was not significantly different that the control organoids nor the APAP only organoids. The general trend of the data was appropriate, suggesting that the liver organoids respond to APAP correctly, and can be rescued by NAC, as patients in the clinic might be.

Urea analysis (FIG. 9) by a QuantiChrom Urea Colorimetric Assay Kit (BioAssay Systems) also showed results with promising trends. Following APAP administration, detected urea decreased as expected. In the control organoids, as well as the APAP+NAC organoids, detected urea production increased over time. There was no statistical significance between groups on day 3 and day 6 (to be expected), nor on day 10, despite the drop in APAP urea production. However, on day 14, both the control organoids and APAP+NAC organoids had increased detected urea levels (p<0.05). As with the albumin data, these trends are appropriate and expected.

Example 2

Glioblastoma (GBM) is a cancer of the brain that despite maximal therapy and surgery infiltrates normal brain and recurs in most patients. Unfortunately, only few 3D in vitro models of GBM exist that faithfully recapitulate the tumor architecture and microenvironment seen in vivo in humans. To address this limitation, we have developed a 3D brain tumor organoid model using a hydrogel that mimics both the composition and mechanical properties of brain extracellular matrix (ECM). The cell lines U138, A172 and U373 were formed into spheroids and encapsulated in hyaluronic acid/gelatin ECM hydrogel. We studied tumor growth, invasion distances and velocities, proliferation, and viability as effects of conditions including Wnt signaling manipulation and different matrix stiffnesses using MTS assays, microscopy, and confocal imaging. WNT modulated environments led to marked decreased migration in U138 spheroids with changes in cell morphology. In different stiffness environments we observed that U373 cells and A172 had increased proliferation in environments stiffer than normal brain tissue, while U138 cell proliferation preferred the native brain elastic modulus. We tested our hypothesis that the cells sense their environment through focal adhesion kinase (FAK) by blocking it with an inhibitor, Defactinib. Following Defactinib treatment, we observed that all the cell lines described above had reverse behaviour in all stiffness realms when FAK was blocked. While not wishing to be bound to any particular theory, this data suggests that tissue and tumor elasticity can serve as a biomarker that has never been used before in clinic to better understand GBM prognosis and direct treatment. Cells may be sensing their environment through FAK phosphorylation. Our results demonstrate that this platform is an effective tool to study environmental manipulations of GBM tumor microenvironment and drug testing. The system may also be used in personalized precision medicine by employing patient-derived cells.

Materials and Methods:

Cancer Organoid Formation:

We used primary Glioblastoma cell lines U-138 MG (ATCC® HTB-16™), U-373 MG (ATCC® HTB-16™) U-87 MG (ATCC® HTB-14™) (obtained from Cell and Viral Vector Laboratory Shared Resource of Wake Forest Baptist Medical Center), U-87ΔEGFR viii cell line (gifted by Dr. Webster Cavenee from Ludwig Cancer Research Institute, San Diego) and A172 (ATCC® CRL-1620™) (obtained from ATCC). Human astrocytes were also constituted in the tumor organoid created so that they can provide a supporting feature to the cancer cells and also recreate the in vivo interaction observed between astrocytes and cancer cell lines. All the primary cancer cell lines were cultured in Dulbecco's Modified Eagle Medium (DMEM)-high glucose added with 10% FBS, 0.5% L-glutamine and 0.5% Pencillin and Streptomycin in 37 degree Celsius incubator with 5% carbon dioxide. Astrocytes were cultured in similar fashion except that Astrocyte media (Thermo Fischer) was used instead of DMEM. The cell lines were trypsinized with 0.5% Trypsin, cells counted and then suspended in the concentration of 500,000 cells per mL of normal media. 10 uL of media added from each cell line ~5000 cells of each cell line (inclusive of astrocytes) were added to each of the wells in a 96 well low adhesion plate (Corning) and cultured for two days in incubator. The organoids were then harvested from these plates to be embedded in gels for our experiments.

Hydrogels:

We used hydrogels-HP from ESI-BIO to create the tumor microenvironment in our system. We chose these gels because they are hyaluronic acid based gels. The components of the gel are thiol modified hyaluronan and Heparin (Heprasil), Thiol modified collagen (Gelin-S) and thiol reactive PEGDA crosslinker (Extralink). Heprasil was dissolved in distilled water and both Gelin-S and Extralink was dissolved in 0.5% photo-initiator. To create the gel, Heprasil, Gelin-S, and Extralink were mixed 2:2:1 by volume.

Figure 20:
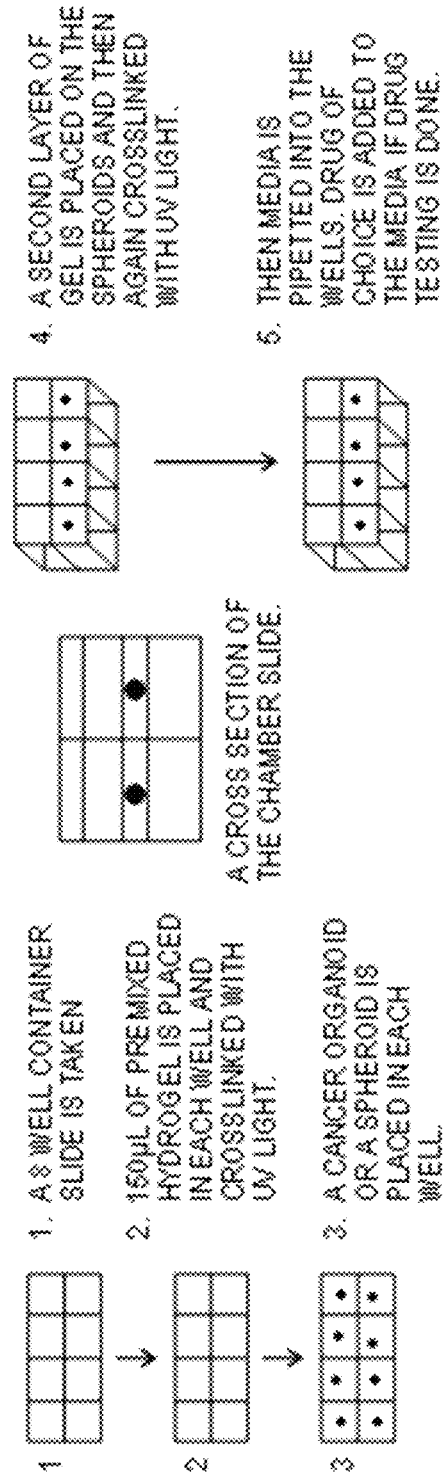
FIG. 20 is a schematic of a method of assembling the 3D organoid model system.

Assembling the System:

An 8-well chamber slide was taken (Nunc™ Lab-Tek™ II Chamber Slide™ System), 150 ul of premixed gel was placed in the wells and then illuminated with UV light for 10 seconds for the gel to crosslink (FIG. 20). A harvested cancer organoid was then placed in each well, covered with 100 ul of premixed gel, and then crosslinked again with UV light (FIG. 20). Next, 300 ul of media was pipetted in to each well and the slides were kept in culture for a week (FIG. 20).

GBM U 138 Spheroid System:

For the WNT experiments, spheroids of GBM U 138 (ATCC® HTB-16™) cell line were formed by hanging drop method in a 96 well plate by using 10,000 cells per drop of 20 μl, which were cultured for 72 hours in high glucose DMEM before being harvested to be setup in HyStem HP-Hydrogels. The spheroids were placed sandwiched between two layers of gel of total volume of 250 μl. The spheroids were then given different media compositions. Normal high glucose media being the control, the spheroids behaviour in WNT pathway agonist BIO and WNT pathway antagonist XAV939 were studied.

WNT Pathway Modulation:

WNT pathway modulation experiments were conducted with our model system.

Experiments were conducted with single cell cancer spheroids with U138 cells. The WNT pathway was manipulated by adding either an agonist of the WNT pathway BIO or an antagonist of the WNT pathway XAV939 to the media. It was observed that the WNT pathway upregulation shut down proliferation and migration in the spheroids, and when WNT pathway was inhibited, the cancer cells' phenotype took on a more epithelial appearance than a mesenchymal appearance.

Figure 10:
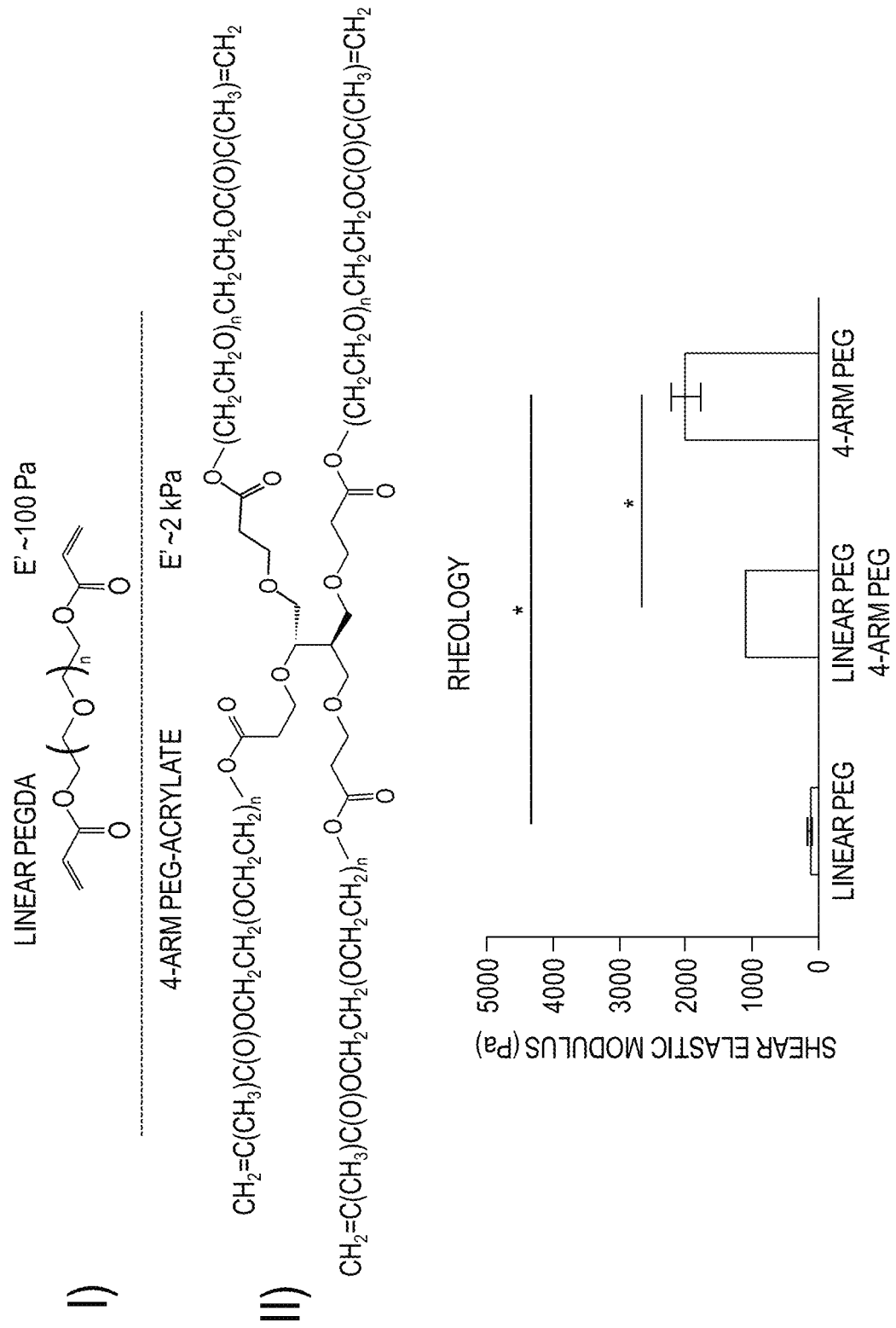
FIG. 10 shows the chemical structure of linear PEGDA crosslinker and PEG-4 ARM crosslinker and a graph of the shear elastic modulus (Pa) of each hydrogel.

Stiffness Studies:

Stiffness experiments were conducted with our cell lines. We have observed that different cell lines respond to stiffness in a different way and that some are sensitive to the stiffness and some are not that sensitive to stiffness. We conducted these experiments in a 2½ D environment by placing the cells on the hydrogels. We manipulated the stiffness of the gels with the cross linker. We conducted the experiments in three different stiffnesses. The three stiffness environment were: (1) S1 —100% Linear PEGDA crosslinker (softest); (2) S2—50% PEG-4 ARM crosslinker and 50% extra link crosslinker (intermediate stiffness); and (3) S3—100% PEG-4 ARM crosslinker (stiffest) (FIG. 10).

Three different primary Glioblastoma cell lines U373, U138 and A172 were used and they were studied separately on a hydrogel with one of the three stiffness measurements listed above. In a 96 well plate, 10,000 cells were placed on 50 μl hydrogel with three different stiffness (stiffness being manipulated through the crosslinker) (9 wells for each stiffness). The cells were in culture for a week in DMEM-high glucose media. MTS assay was done on day 1, 4 and 7 to measure the number of viable cells in each environment.

In addition, three different primary Glioblastoma cell lines U373, U138 and A172 were used and they were studied separately on hydrogel with one of the three stiffness measurements listed above. In a 96 well plate, 10,000 cells were placed on 50 μul hydrogel with three different stiffness (stiffness being manipulated through the crosslinker) (9 wells for each stiffness). The cells were in culture for a week in DMEM-high glucose media and media along with 100 nm Defactinib for FAK phosphorylation inhibition studies. MTS assay was done on day 1, 4 and 7 to measure the number of viable cells in each environment.

From these stiffness experiments, it was observed that the U373 cells and A172 cells proliferated better on the soft hydrogels rather than the stiffest (S3) when in the presence of Defactinb, whereas, in the absence of Defactinb, the U373 cells and A172 cells preferred the stiffest hydrogel (S3).

The results demonstrate that some GBM cell lines are sensitive to stiffness and this can affect their proliferation. The cells may sense this stiffness through FAK phosphorylation. Without wishing to be bound to any particular theory, inhibition of FAK phosphorylation may change the stiffness perception of cells and in turn change their behavior.

Figure 11:
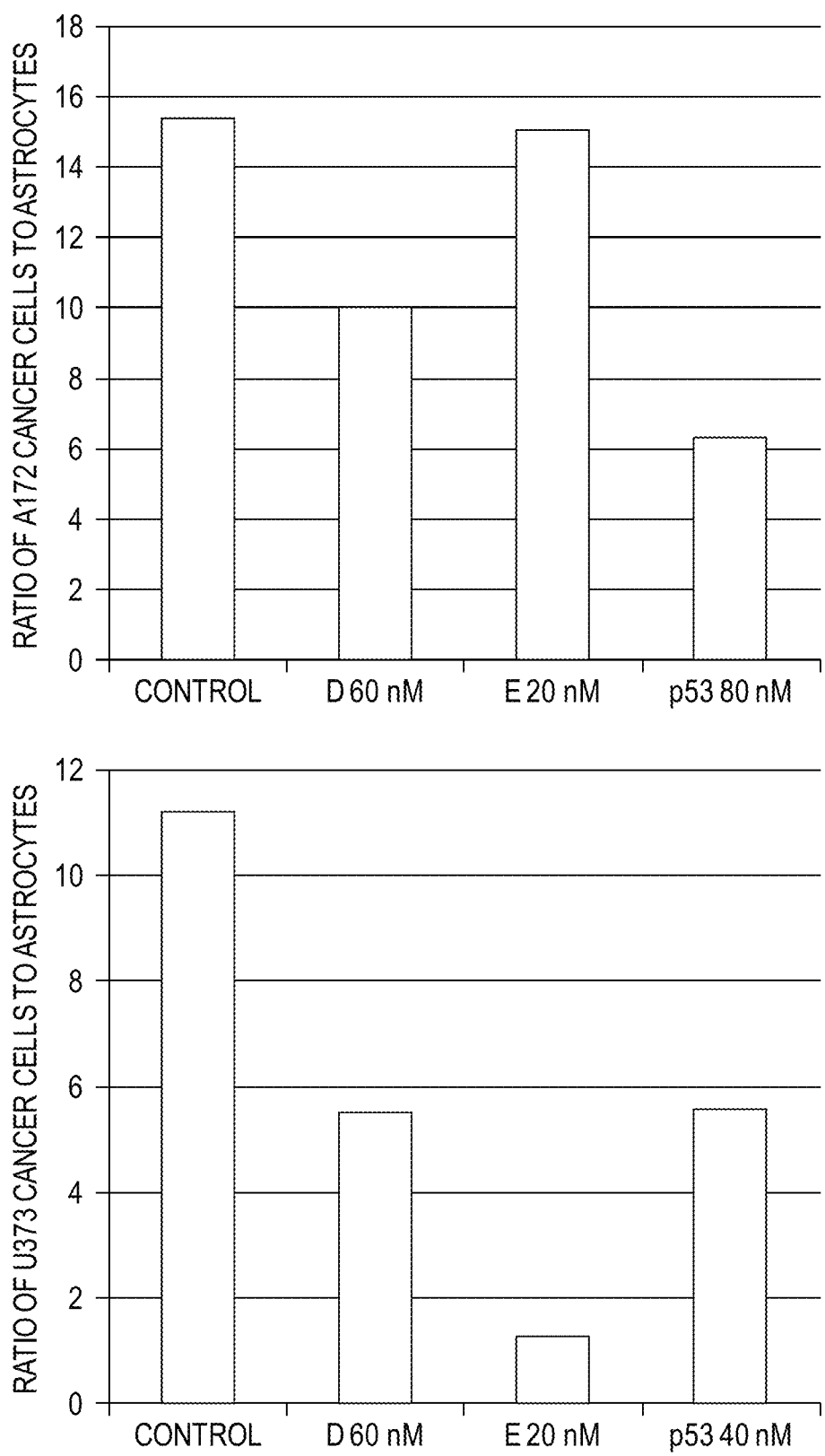
FIG. 11 shows graphs of the ratio of cancer cells to astrocytes. The top graph shows the ratio of A172 cancer cells to astrocytes as calculated by the MATLAB program using the confocal images. The bottom graph shows the ratio of U373 cancer cells to astrocytes as calculated by the MATLAB program using the confocal images.

The same experiments are conducted with multicellular spheroids. The cell lines used for generating a multicellular spheroid of GBM are U87 (wt-EGFR), U87 (ΔEGFR), U138, U373 and A172 along with astrocytes. Each cell line is stained with a distinct membrane dye (cell tracker and Qdots) so that they can be identified in the spheroid. The cell lines used have different mutations (Table 2) between them making it a heterogenous tumor mass. The cell lines chosen thus encompass all the mutations that are observed in different types of GBM molecular subtypes: Proneural, Neural, Classical and mesenchymal. FIG. 11 show graphs of the ratio of A172 or U373 cancer cells to astrocytes.

TABLE 2

Mutations in cell lines for the multicellular spheroids.

| Cell lines | Mutations |
| --- | --- |
| A172 | CDKN2A, PTEN and EGFR (190 Kda mutation) |
| U87 | CDKN2A, NF1 and PTEN |
| U138 | P53* and EGFR upregulation. |
| U373 | P53* and EGFR upregulation. |
| U87 (ΔEGFR) | EGFR VIII (2-7 Deletion mutation) |

Example 3

In a 96 well plate, we placed 10,000 cells on two sets of nine wells of 50 ul PEGSSDA hydrogel and the wells were filled with DMEM high glucose and cultured for a week. On day 4, one set of gels were softened using NAC 100 mmol for 60 minutes. Now proliferation of cells was compared between control gels and softened gels using MTS assays on day 7.

In a 96 well plate, we placed 10,000 cells on two sets of nine wells of 50 ul S3 stiff hydrogel and the wells were filled with DMEM high glucose and cultured for a week. On day 4, one set of gels were softened using collagenase (1:10 dilution) for 10 minutes. Now proliferation of cells was compared between contol gels and softened gels using MTS assays on day 7.

The results demonstrated that the stiffness sensitivity of the cells could be harnessed as a therapeutic option in the treatment of GBM. Reduced proliferation was seen in gels softened with NAC. To adapt it more clinically, collagenase was used to soften the gels and the same results were observed.

Example 4

A GBM model platform was developed using a brain-like HA matrix biomaterial, with which 3D GBM organoids comprised of multiple cell populations were created. This system has been used to assess anti-cancer drugs in vitro (FIG. 11), demonstrating that different GBM cell populations display distinct drug responses. To date we have created GBM organoids comprised of up to 5 different cell types, representing the 4 subtypes of GBM as well as astrocytes. We have employed these organoids to investigate how the physical tumor microenvironment (TME) parameters influence population drift over time. We manipulated the stiffness of the TME to mimic sub-brain stiffness, typical brain stiffness, or increased stiffness that is observed in many brain tumors, and used fluorescent tags to track each cell population over time. Accordingly, we found that particular subtype representatives responded favorably to stiffening TME, while others receded. This demonstrates how subtype composition may "drift" during tumor evolution. With this platform, we are able to directly observe various tumor clones in a 3D, brain-like microenvironment. This represents a distinct advantage over the most advanced conventional approach of PDX by enabling not only qualitative, but also quantitative assessment of individual subclone contribution to the overall tumor.

Figure 12:
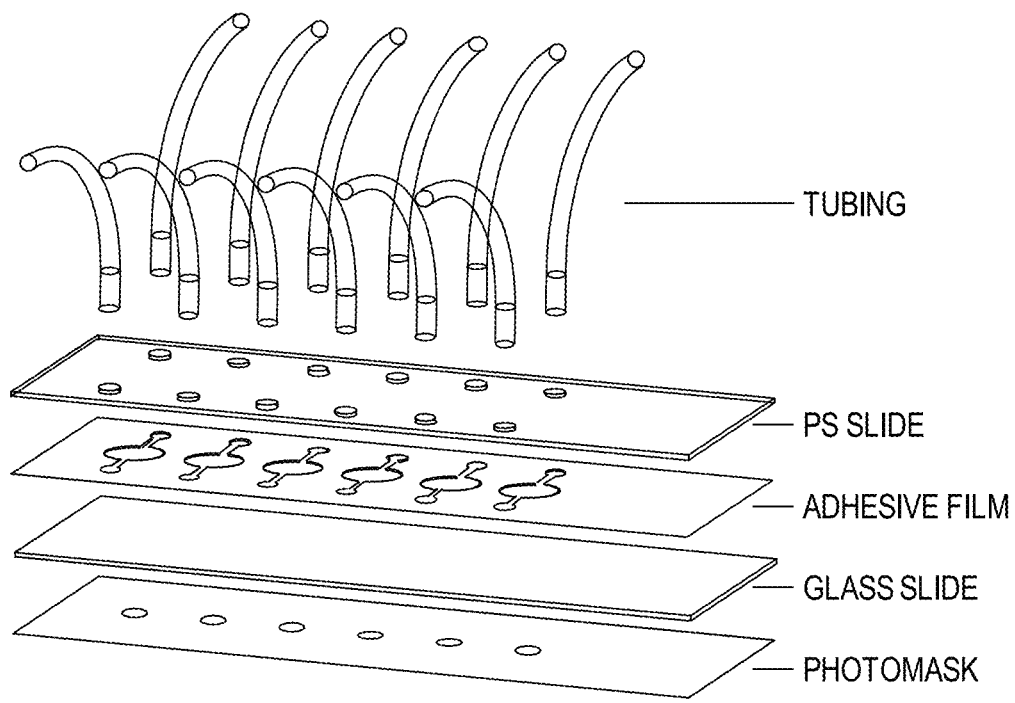
FIG. 12 is a schematic of a system of the present invention; a) shows assembling of microfluidic device layers; b) shows in situ patterning: a microfluidic chamber (i) is filled with hydrogel mixture containing HA hydrogel, photoinitiator, and cells (ii) and exposed with UV illumination through a photomask (iii) exposed hydrogel is crosslinked (iv) and clean buffer is used to flush non-crosslinked gel (v) flushing buffer is replaced with media (vi) for incubation; and c) shows the total measurement set-up, featuring a low-volume, closed loop fluidic circuit for each organoid facilitated by a computer-controlled peristaltic pump.
Figure 12:
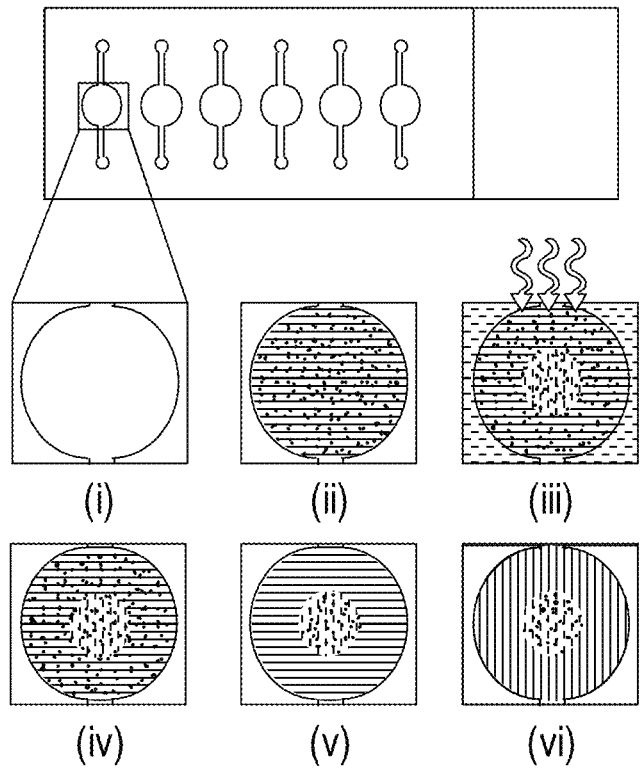
Figure 12:
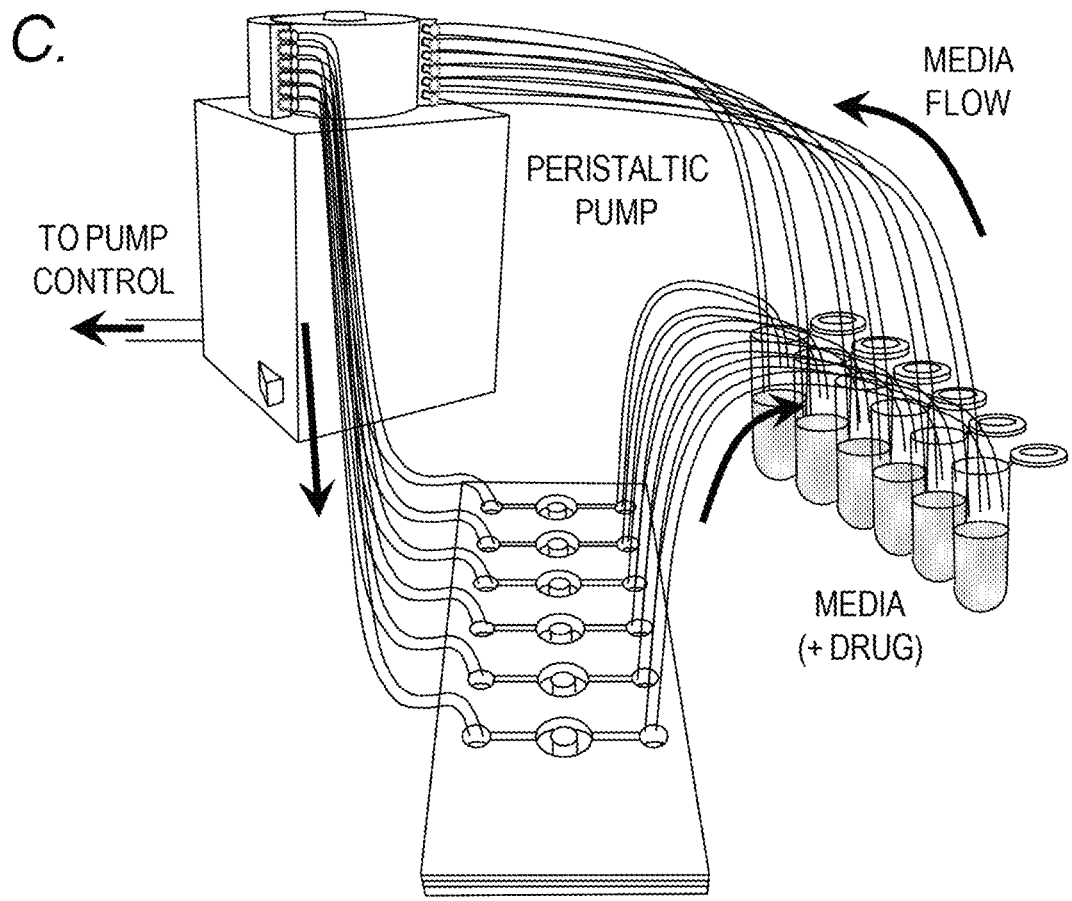

Patient-Derived Tumor Organoids: Biofabrication, Take Rate, and Viability:

To address the challenges of integrating 3D organoids within microfluidics, we have developed a methodology for in situ biofabrication (FIG. 12) that utilizes a HA and gelatin-based hydrogel, HyStem, that has been employed extensively in tissue engineering, and biofabrication approaches. In the general approach to fabricating tissue constructs, HA and gelatin/collagen components are mixed with cells, as well as a crosslinker and photoinitiator to support thiol-acrylate photopolymerization. Each cell-gel precursor is introduced to the microfluidic chambers sequentially and patterning is accomplished using a positive-tone photomask to define shape and location of constructs. The cross-linked hydrogel is adherent to the top and bottom surfaces of the chamber, allowing it to be retained under fluid flow. This patterning can be performed in an arbitrary number of independent microfluidic chambers. The resulting 3D constructs can subsequently be kept under circulating flow with long-term viability, and the total system is amenable to analytical investigation, including both biochemical assays and direct imaging on chip. Additional patterning (e.g. with additional cell types) can be used to produce multi-component structures, enabling significant system complexity. Notably, the hydrogel also supports incorporation of solubilized ECM, supplying additional biomolecular factors specific to each tissue type. Overall, this approach is rapid, inexpensive, and modular, with potential to be mass-produced for a large number of parallel experiments, and consistently results in viable tumor organoids that are available for drug screening studies.

Conventional 2D culture performs poorly in supporting patient-derived cancer cells in vitro, typically yielding take rates below 25%. Even PDX models using the most aggressive tumor biospecimens are successful only 25-33% of the time. This poor take rate reduces the utility of PDX for most cancer patients and limits real-time availability of results for clinicians. In contrast, our system has rapid turn around and yields a take rate >90%. In addition, the platform has been employed in drug screens, demonstrating that the tumor organoids maintain the selective responses to drugs observed in patients. To date, we have created sets of patient-specific organoids from a diverse group of primary tumors and their metastatic sites (see below) including colorectal cancer, peritoneal mesothelioma, extremity sarcoma, and high- and low-grade appendiceal metastases (to omentum, ovary, and liver).

The central challenge in conventional cancer treatment design is that there is only one reliable test bed: the patients themselves. Most often, a treatment is administered based on statistical likelihood of success in the broader population, and actual effectiveness in a particular patient is assessed only after the fact. In patients with intrinsic or acquired resistance to the treatment, this results in further growth of the tumor and a loss of critical treatment time. Additional drugs can then be investigated, but only serially and with each one still being a "best guess" with diminishing probabilities of success. Moreover, during this time, due to spontaneous changes, and in response to treatments, the tumor is evolving—potentially with changes in drug responsiveness. An ideal solution would be a method by which a tumor could be probed outside of the patient, where multiple candidate treatments could be investigated in parallel to determine effectiveness without loss of time or potential harm to the patient. Initially, animal models seem attractive because they could provide complexity reminiscent of the in vivo tumor physiology. However, even beyond infrastructure requirements and ethical questions that accompany the use of animals, the power of these models to predict outcomes in humans is tenuous. Moreover, patient-derived xenografts have unsatisfactory take rates, and have only been successfully established using the most malignant of tumors.

In vitro 2D cultures have been a laboratory workhorse, but fail to recapitulate in vivo tissue, but 3D culture has been shown to capture a more faithful reproduction of the physiological microenvironment. The 3D organoid biofabrication within the GoC devices yields three important points of innovation. 1) The unique microfluidic device fabrication method provides inexpensive, easy to fabricate TOC devices that support parallel production, addressing, and analysis of patient-specific cell constructs in microenvironments that closely resemble in vivo conditions. 2) Tissue-mimicking ECM hydrogels create a better TME than many common biomaterials (collagen, alginate, PEG, etc.) and provide reliable take rates when incorporating even the most difficult to maintain biospecimen-derived tumor cells. Notably, take rates for this platform in preliminary studies have been >90%, while those of PDX and 2D culture models are generally 25-33% and below 10%, respectively. 3) The capability to use patient tumor biospecimens in an ex vivo model for in vitro probing of drug response and tumor evolution, thus providing insight for designing patient-specific therapies.

Figure 13:
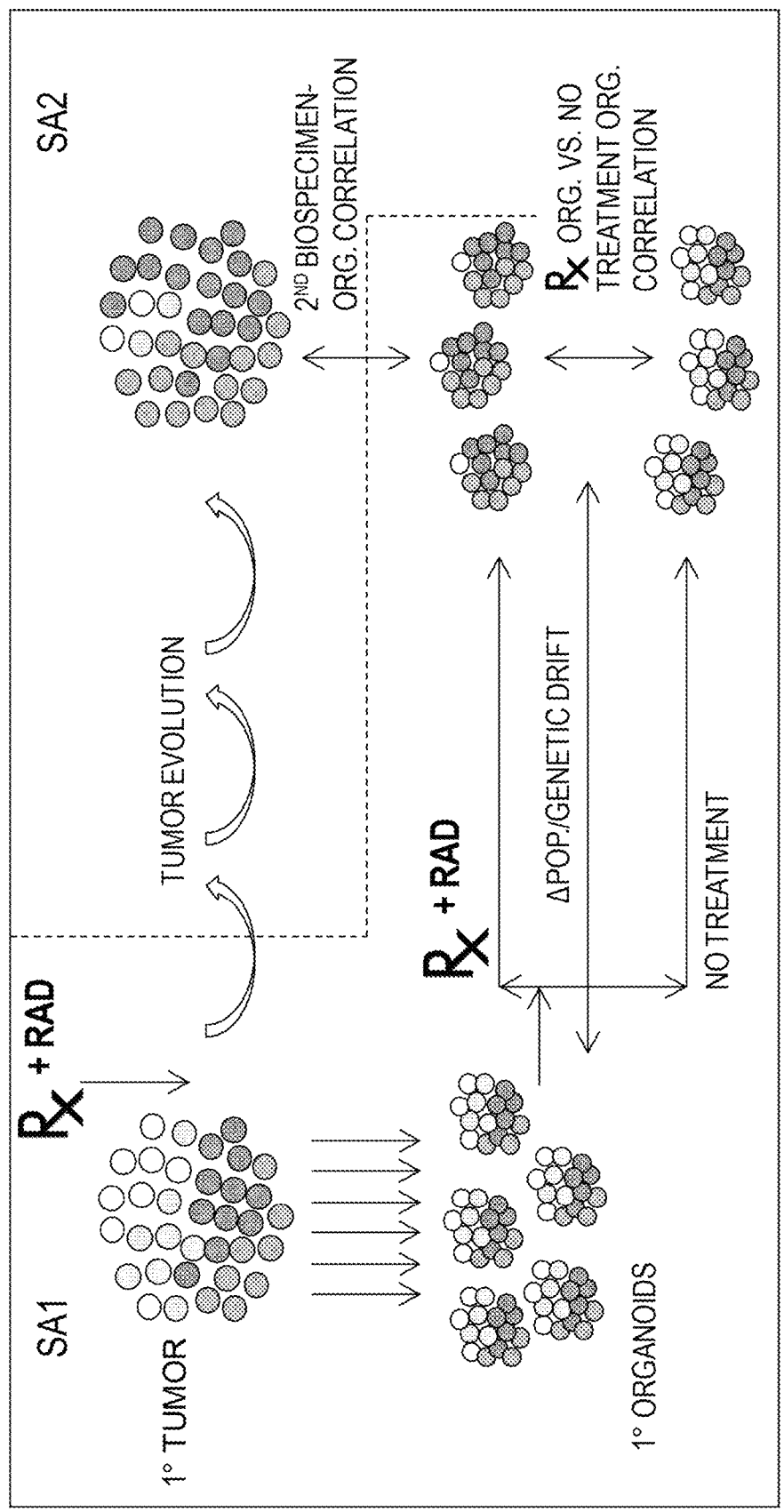
FIG. 13 is a schematic of an example GBM model system with SA1 focusing on evaluating how GBM subtype heterogeneity (genotype and phenotype) evolves over time with and without identical treatments to corresponding patients, and SA2 focusing on the comparisons between the GBM organoid model screening studies with patient outcomes, thereby building a correlative dataset with which we may be better oriented to design therapies for these patients.

The overall goal of this research is to pair bioengineering technologies with patient-specific biology, thereby enabling a GBM model that faithfully reproduces the dynamic changes of in vivo tumor heterogeneity and allows quantitative assessment, probing, and drug screening. This research capability will offer a route to therapy optimization that could drastically improve personalized oncology for patients with GBM. Individual aspects of the model system have already been demonstrated and tested with other patient-derived cells; here we propose to deploy the platform for GBM. FIG. 13 describes the overall approach.

General Approach Methodology:

Specimen Acquisition: Ex vivo model development has been performed at the Comprehensive Cancer Center at Wake Forest through the Wake Forest Brain Tumor Tissue Bank (WFBTTB). This biorepository contains patient-derived glioma tumor specimens from over 862 glioma patients including both low- and high-grade specimens obtained over the past decades. The WFBTTB is maintained through the Tumor Tissue and Pathology Shared Resource, IRB approved protocols CCCWFU 99A-98 & 01403. All patients who contribute specimens sign HIPAA waivers of consent and all specimens will be coded to prevent access to patient identity.

Figure 14:
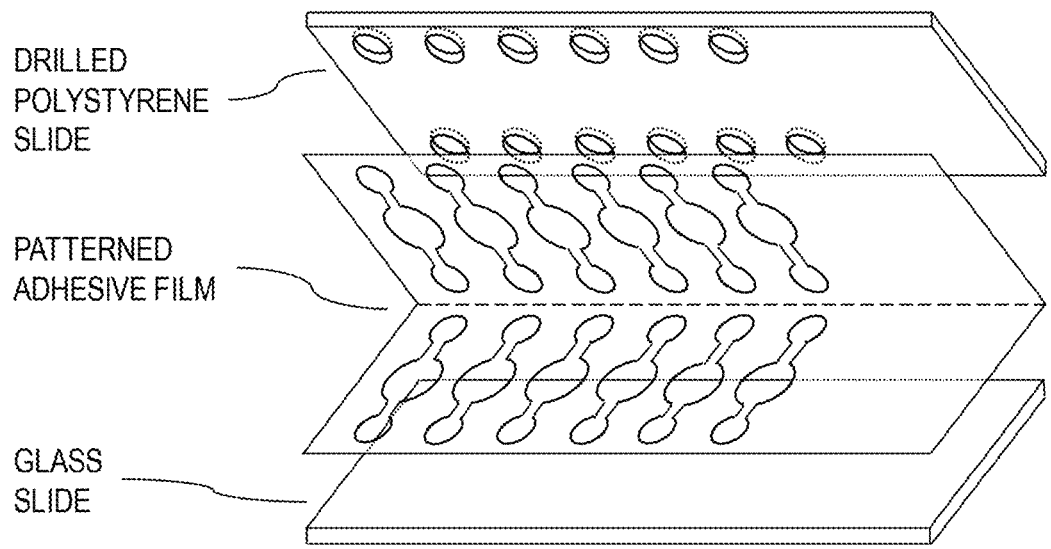
FIG. 14 is a schematic of device fabrication in which patterned adhesive films are layered between a glass slide (bottom) and a polystyrene slide drilled with fluid inlets and outlets (top) to form microfluidic channels.

Microfluidic device fabrication: Conventional use of lithographically-defined polydimethylsiloxane elastomer for prototyping microfluidic devices can take days due to reliance on expensive transparency masks, photolithography for device definition, serial casting, and precise layer alignment. This presents a challenge to scale up and clinical translation. However, this approach is necessary only for extraordinary resolution (~1 μm). Our 3D systems enable use of somewhat larger-scale but considerably simpler thin, patterned adhesive films that can be self-aligned and layered through folding to form microfluidic structures (FIG. 14). This removes the need for cleanroom processes and definition can be achieved through the use of a computer-controlled razor plotter or laser cutter. Lateral device definition in these structures is limited to ~200 μm while depth is defined by thickness of adhesive film layers used (~100 μm). These dimensions are sufficient to support sub-microliter fluid handling and constructs containing populations of cells relevant to faithful tissue modeling. Using this platform, we have produced a number of complex structures commonly made in PDMS, including valves, mixers, and other functional systems for microfluidic circuits. Additionally, our system allows for creation of microreactor chambers with an average volume of 7 μL, thus requiring less than 100 μL of media total for a 6 organoid system and its connecting channels.

Figure 15:
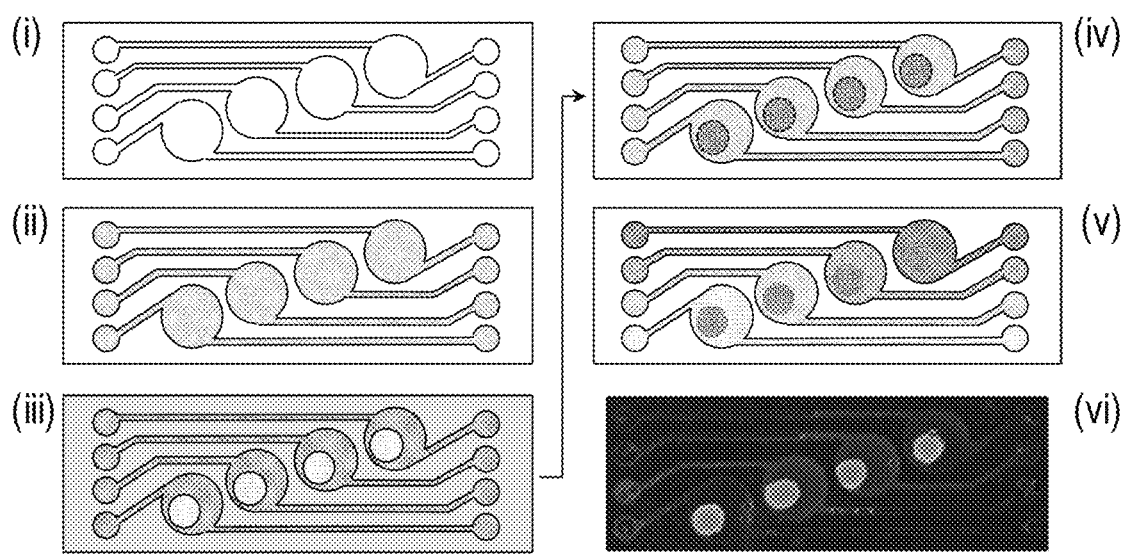
FIG. 15 is a schematic of in situ 3D cell culture microconstruct formation workflow. Channels (i) are filled with a mixture of photocurable hydrogel precursor, cells, and additional components (light red, ii). A photomask (grey) is employed to define construct shape (iii). Following UV exposure, cross-linked hydrogel (dashed lines) are formed in the channels (iv) and the remaining solution is replaced with clean buffer (v). Epifluorescence imaging (vi) demonstrates construct formation.

Organoid-device integration: As described above, HA and gelatin/collagen components are mixed with biospecimen-derived cells, as well as a crosslinker and photoinitiator to support photopolymerization in situ within the devices. Cells are added to the gel precursor preferably at a density of 20 million cells/mL or higher, after which the cell-gel mixture introduced to the microfluidic chambers sequentially and patterning is accomplished using a positive-tone photomask to define shape and location of constructs (FIG. 15). The resulting 3D constructs are typically maintained under circulating flow at 10 μL/min with long-term viability.

Genetic analysis of biospecimens and organoids: Clinical Genomic Sequencing: The Wake Forest University Comprehensive Cancer Center Cancer Genomics Shared Resource has an ongoing collaboration with Foundation Medicine and an active Precision Medicine Platform (CCCWFU 01403), which supports genomic sequencing of patients, including all glioma patients at the CCCWFU. Over the past year, approximately 52% of new GBM patients seen at the WFBCCC have undergone genomic sequencing through this protocol. Genomic data is stored in a clinical database maintained by the Brain Tumor Disease Oriented Team. This institutional registry contains clinical, histopathologic, radiographic, and treatment characteristics for all brain tumor patients treated at the Wake Forest Baptist Comprehensive Cancer Center (CCCWFU 01516, PI: Strowd). This clinical registry will be leveraged to provide access to genomic profiles and clinical and treatment data in real time for all patient specimens at diagnosis and throughout the patient's treatment course.

DNA and RNA will be purified from the source tumor tissue and from organoid pellets using standard methods (AllPrep kit, Qiagen). RNA from the tumor and organiods will be archived to allow for future gene expression studies. While gene panels (e.g. Foundation Medicine) focus on the most common genes mutated in cancer, we will perform whole exome sequencing to capture potential novel changes outside the subset of cancer panel genes. Exome sequencing will be performed using the Illumina TruSeqRapid exome sequencing protocol to a minimum depth of 200× using 150×150 bp paired-end (PE) sequencing in the Wake Forest Baptist Comprehensive Cancer Center (WFBCCC) Cancer Genomics Shared Resource (CGSR). Next Generation DNA sequencing (NGS) will be performed and all raw NGS data will undergo rigorous QC (FASTQC). Raw fastq files will be generated by four different lanes using the illumina TruSeq Rapid Exome Library. For each fastq file, it will be aligned to reference (hg19) by BWA mem, with version bwa-0.7.12.

The preprocessing for somatic mutation calling includes duplicate mark by Picard (https://broadinstitute.github.io/picard/), indel realignment by GATK 3.6 (https://software-.broadinstitute.org/gatk/), and base recalibration by GATK 3.6. This preprocessing will be implemented for each sam output from BWA. For each sample, the four aligned bam files are merged as the final bam by Samtools 1.3.1, after adding read group (RG) information into each aligned bam file during preprocessing. The somatic mutation calling will be implemented by MuTect1-1.1.4, VarScan2-2.3.9, and Somatic-SNIPER. The somatic mutation loci and genes for each sample will be combined from the outputs of the three pipelines for somatic mutation calling. To specify the tumor purity for the VarScan2, we will utilize AbsCN-seq software. The estimated tumor purities will be compared with those from pathologists.

The following three categories of genetic profiling will be focused on:
1. Drift in TCGA subtype (Verhaak et al., Cancer Cell 17, 98-110 (2010)) (neural, proneural, mesenchymal, classical) looking at the genes associated with these phenotypes to see if tumors evolve into a different subtype combination
   a. Proneural: IDH1/2, TP53, PDGFRA, PIK3CA, PIK3R1, DLL3, NKX2-2, SOX2, ERBB3, OLIG2
   b. Neural: NEFL, GABRA1, SYT1, SLC12A5, FBXO3, GABRB2, SNCG, MBP, ERBB2
   c. Classical: EGFR, CDKN2A, FGFR3, AKT2, NES, RB1, CDK4
   d. Mesenchymal: NF1, RB1, PTEN, CASP1/4/5/8, ILR4, CHI3L1, TRADD, TLR2/4, RELB
2. Drift in TMZ-resistance genes including but not limited to PHF6 (Hiddingh, et al., *Sci Rep* 4, 5260 (2014))
3. Mutations associated with treatment resistance including:
   a. Development of hypermutation (Hunter et al., *Cancer Res* 66, 3987-3991 (2006): patterns of developing a hypermutated genotype at recurrence may be determined/predicted. This has been associated with TMZ resistance and a more aggressive pattern.
   b. Genes associated with TMZ-resistance: AKT2, DDIT4, ERBB2, MTOR, NF1, PDFRA, PIK3CA, PIK3R1, PTEN, TSC1, CDKN2A, CDK4, CDK6, RB1.

Deployment of Multi-Clonal, Patient-Derived Ex Vivo GBM Tumor Organoid-On-a-Chip Systems to Quantify Genetic and Phenotypic Diversity Drift.

To our knowledge, there are no 3D systems that accurately recapitulate GBM in vitro within a brain-like ECM environment. This is particularly true with respect to incorporation of the four GBM subtypes that each feature unique genetic and phenotypic profiles. We will address this challenge by dissociating patient GBM biospecimens, sorting them into unique sub-clones by subtype, and label each with distinct fluorescent tags. We will then recombine them in their original ratios into 3D tumor organoids with a brain ECM mimic. Temporal variation in population (i.e. change in fluorescent subpopulations) and genetic profile will be compared between organoids receiving treatment and no treatment.

Figure 16:
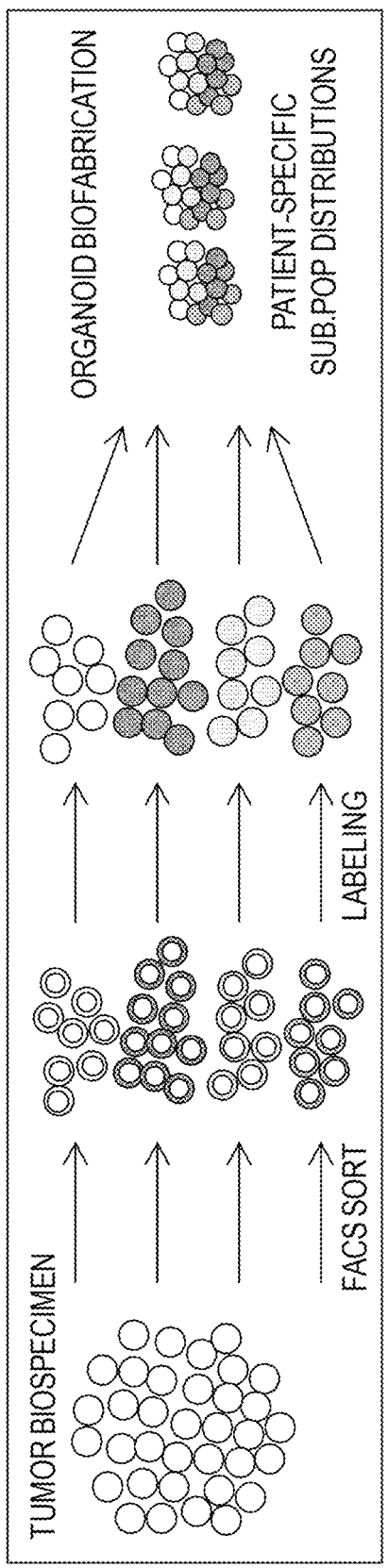
FIG. 16 is a schematic showing the workflow of biospecimen dissociation, sorting, labeling, and recombination in organoids.

Methods:

Cell processing from biospecimens (FIG. 16): Fresh tumor biopsies will be minced, washed, digested, and filtered to yield cell suspensions. While, we have used 12-hour incubation in DMEM+collagenase/hyaluronidase for solid GI tumors, brain tissue requires less incubation time (approximately 2-6 hours) due to lower collagen content.

Figure 17:
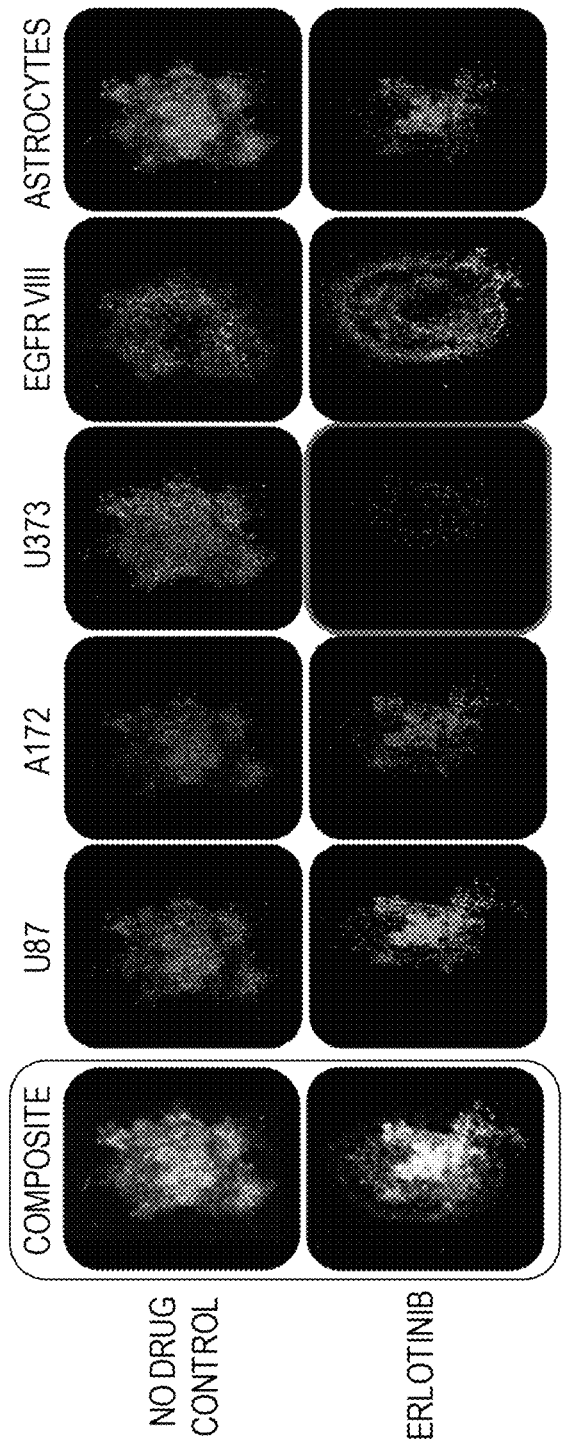
FIG. 17 shows images of organoids comprising 5 different cell types that are each labeled with a different detectable compound so that each cell type can be optically distinguished in the organoid.

Resulting cells will be labeled and FACS sorted according to GBM subtype surface markers (described above). FIG. 17 shows images of an example organoid comprising 5 different cell types with each cell type being labeled with a different detectable compound so that each cell type can be optically distinguished in the organoid. Following sorting, fluorescent signals can be intensified through matching membrane-incorporating dyes with wavelengths of FACS antibody for increased tracking capabilities. We will employ CellTracker™ CM-DiI Dye, Qtracker® 525 Cell Labeling Kit, Qtracker® 655 Cell Labeling Kit, Qtracker® 705 Cell Labeling Kit, and Qtracker® 800 Cell Labeling Kit to enable tracking of each independent subpopulation.

Figure 18:
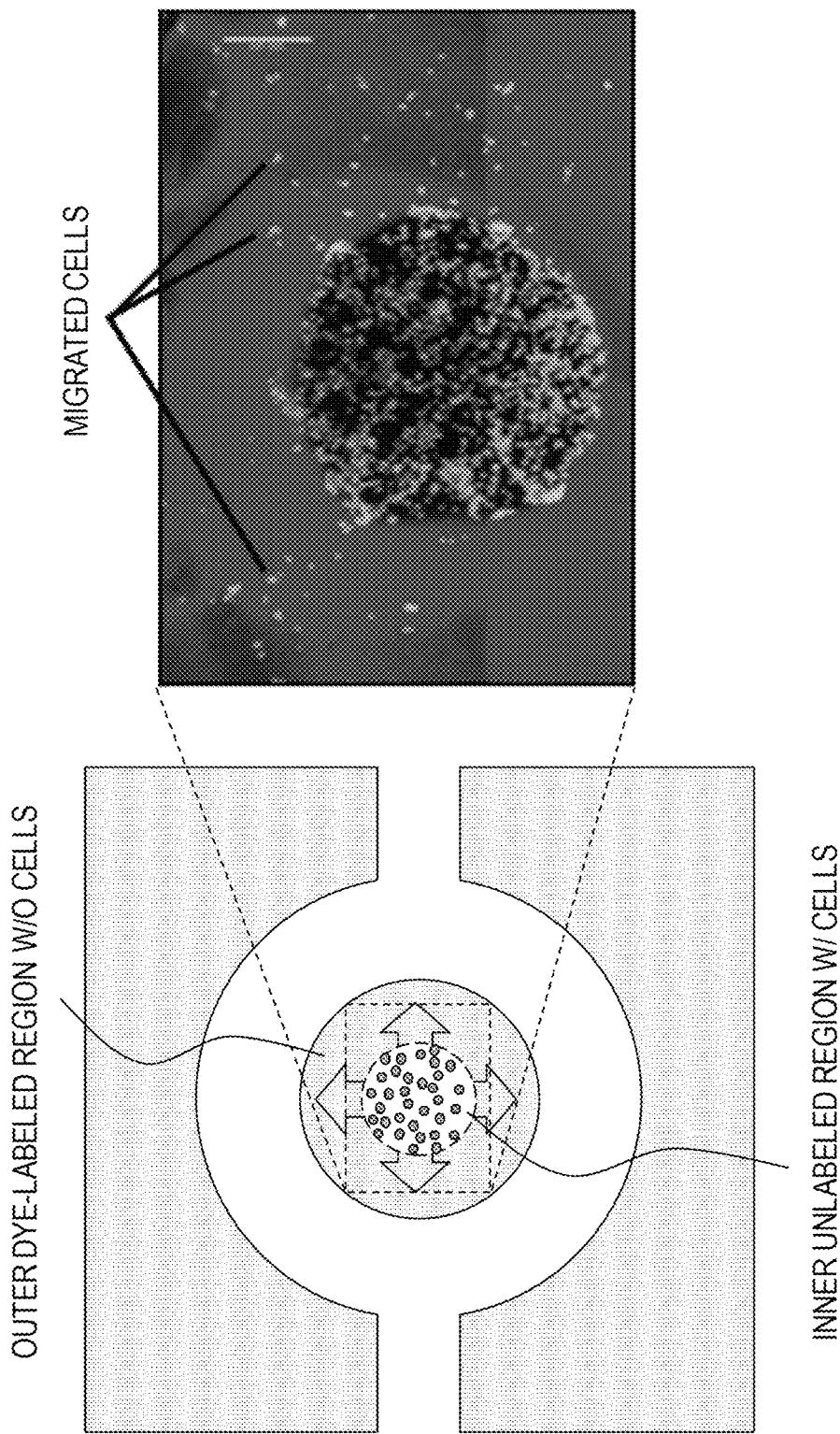
FIG. 18 is a schematic of an example concentric GBM-brain tissue organoid in a microfluidic chamber, and shows green-labeled patient biopsy-derived mesothelioma cells migrating out of an unlabeled central tumor core into a red-labeled brain matrix.

GBM-brain-relevant organoid spatial biofabrication: Following cell processing/labeling, cells will be recombined to emulate the in vivo ratio of subpopulations, thus promoting patient-specific tumor heterogeneity. Using the two-step in situ biofabrication approach described above and in FIGS. 18 and 19, the tumor core will be created in the GoC using a HA-rich, brain matrix mimic (i.e. matched composition and stiffness). Around this core, an additional concentric brain matrix will be produced to allow improved imaging and tracking of tumor cell invasion. For simplicity, the surrounding region will initially be cell-free, but additional cell types (neurons, astrocytes, glial cells, endothelial cells, etc) can be integrated as necessary due to the straightforward nature of the biofabrication approach.

Patient-specific drug treatments: Standard of care treatment of newly diagnosed GBM includes conformal radiation therapy (54.90-60.00 Gy) with concurrent daily oral temozolomide (TMZ, 75 mg/m$^2$/day) followed by adjuvant oral TMZ in a 5-day-on/28-day treatment cycle (150-200 mg/m$^2$/day) for a total of 6 cycles. 1-year survival rates of approximately 70% are observed with this treatment, with median progression-free survival of 7 months. Pharmacokinetic studies in both human and non-human primates show that TMZ concentrations in the cerebrospinal fluid (CSF) reach approximately 20% of those in plasma with peak CSF concentrations of 26±4 μM. This level of drug and radiation exposure serves as an initial framework, but is modulated patient to patient. To drug treatment will be repeated in $T_1$ organoids to assess drug response shifts.

Viability assessment: Cell viability will be quantified directly, allowing the anti-proliferative and pro-apoptotic effects of the treatments to be determined. Specifically, efficacy of drug treatments will be determined as follows; Specifically, viability of cells will be assessed by LIVE/DEAD (number of viable cells alone, number of viable cells versus dead cells), mitochondrial metabolism (MTS), LDH quantification (positive in tumor cells), and IHC (apoptotic vs. proliferative markers).

Population evolution and genetic drift analysis: Population evolutions and genetic drift will be assessed in several ways. First, macro-confocal imaging (Leica TCS LSI) will be used to generate single channel and composite z-stacks and 3D maximum projects of each organoid and the multiple labeled populations within. Comparison between $T_0$ and $T_1$ will allow for quantitative assessment of the particular subtype populations contributing to the organoids. Importantly, since the imaging is non-invasive, we will also have a series of sequential data points between T0 and T1, allowing a very nuanced inspection of population changes. Importantly, this gives much more opportunity for data collection than other current models such as PDX. Second, genetic analysis will yield 2 primary sets of data. 1) We will focus on the 4 subtypes and the genes associated with them. We suspect this data will provide a more nuanced supplement to the visual tracking data above. 2) We will use overall genetic expression clustering from the whole exome to look for general patterns between organoid time points. This can then in turn identify other expression profiles and mutations that until now were perhaps overlooked.

Comparison of Ex Vivo Genetic and Phenotypic Drift with Secondary Surgery Samples.

No in vitro model has thus far been able to accurately capture the dynamic variations of GBM subtype populations observed in patients. After in vivo patient tumors and ex vivo organoids have evolved in parallel, we will determine differences in their genetic profile, composition, phenotype, drug response, and 3D invasion potential. These assessments will allow direct comparisons of genetic indications, manifested phenotypic expression/behavior changes, and population evolution over time.

Figure 19:
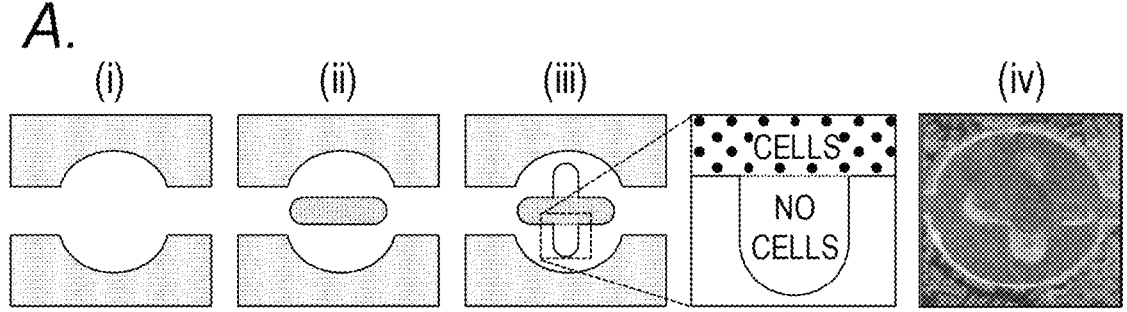
FIG. 19 shows schematics for in vitro cell migration analysis; panel A shows a schematic of construct fabrication in a microfluidic chamber, which (i) involves definition of an oblong cuboid structure containing cells (red dots), ii), followed by a perpendicular and intersecting cuboid (white), iii) to form a cross-bar architecture (optical micrograph), iv); panel B shows fluorescent micrographs of crosses containing mCherry HTC116 cells under circulating flow of clean buffer across four days; migrating cells (i.e. those that cross into the cell-free region) are false-colored yellow; and panel C shows migration histograms of panel B, showing distance traveled into the cell-free region on day 1 (red), 2 (green), and 3 (blue).
Figure 19:
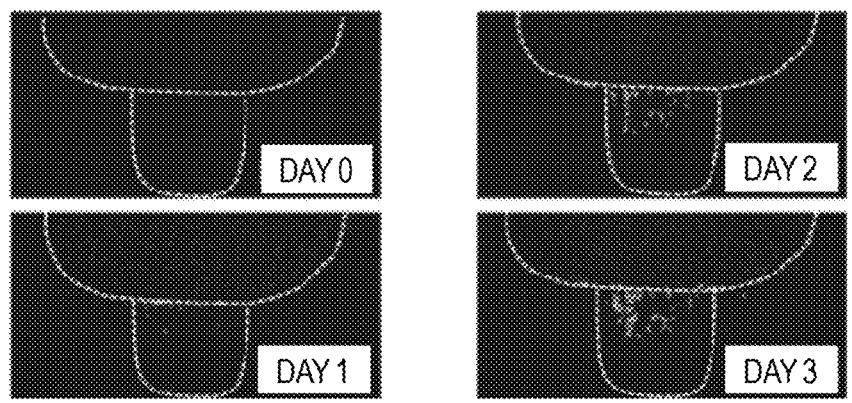
Figure 19:
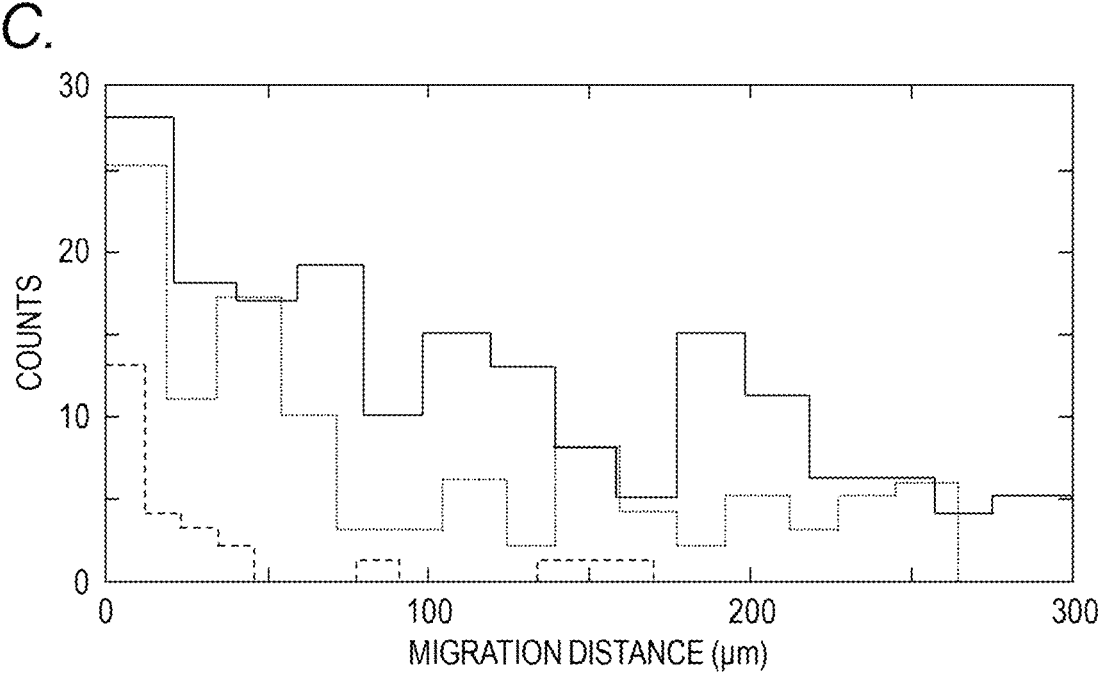

Engineered Tumor-on-a-Chip 3D Invasion Assessment: The second critical value enabled by staining will be quantifiable cell migration. This will be compared subsequently to the metastatic outcomes of the patients with the expectation that constructs derived from patient tumors that metastasized to additional sites will have significantly higher migration under drug exposure than those that did not. Achieving both viability and migration assessment in a single device is not trivial and represents an additional innovation of this project. For this, we have developed a novel, two-step fabrication approach, outlined in FIG. 19. First, hydrogel precursor mixed with cells is injected to the chamber and photopatterned into an oblong cuboid. Next, identical hydrogel precursor without cells is injected and patterned into another oblong cuboid, perpendicular to and intersected by the first. The end result is a cross-bar architecture in which cells are localized to one arm, but able to migrate through a discontinuity-free interface with the remaining arms. Because of this structure, the border between intersecting regions is easily inferred from the construct borders (see FIG. 19, panel A), providing a point of reference. In support of this project, we have performed preliminary measurements with the proposed construct, utilizing HTC116 cells that express the fluorescent reporter mCherry as a demonstration vehicle. FIG. 19, panel B shows sequential images of cells in a cross-bar structure after four days of circulating DMEM flow. Migrating cells, defined as cells that have crossed the border (dashed line), are indicated in yellow. A larger number of cells migrate on average farther out of the cellularized region each day (FIG. 19, panel C). Here, mCherry expression offered the ability to follow migration over time. While LIVE/DEAD staining will instead offer a snapshot on the final day of the experiment for patient cells, this still allows sufficient quantification of migration, ultimately delivering both total number of migrating cells and mean distance travelled as metrics. As a further improvement, we have also recently employed the same measurement mechanism in a modified concentric architecture (FIG. 18), more closely representing tumor shape. In this case, the border between cell-free and cell-rich regions can be identified through selective labeling of hydrogel with a covalent Alexa Fluor dye.

Patient tumor population evolution and genetic drift analysis: Re-resection biospecimens will be 1) sorted by FACS as described above and 2) genetically queried as described above.

Patient tumor population and organoid comparisons: Comparison between treated tumor organoids and untreated tumor organoids and comparisons between re-resection biospecimens and organoids will be a combination of genetic and phenotypic assessment as described above. Additionally, comparison between treated tumor organoids and treated patients from which re-resections are made available at a second surgical event will be performed in similar manner.

The foregoing is illustrative of the present invention, and is not to be construed as limiting thereof. The invention is defined by the following claims, with equivalents of the claims to be included therein.

That which is claimed is:

1. An artificial cell construct comprising:
    a core comprising glioblastoma cells and a first population of non-cancerous tissue cells that comprises glial cells, wherein the glioblastoma cells and the first population of non-cancerous tissue cells are intermixed with one another; and
    a shell comprising a second population of non-cancerous tissue cells that comprises endothelial cells, wherein the shell surrounds the core.

2. The construct of claim 1, wherein the glioblastoma cells comprise at least two different glioblastoma subtypes or are representative of different glioblastoma subtypes.

3. The construct of claim 1, further comprising a third population of non-cancerous tissue cells that comprises astrocytes.

4. The construct of claim 1, wherein said glioblastoma cells are selected from the group consisting of U138MG, U373MG, U87MG, A172 glioblastoma cell lines, and any combination thereof.

5. The construct of claim 1, wherein said glioblastoma cells are labeled with a first detectable compound and said first population of non-cancerous tissue cells are labeled with a second detectable compound, and wherein said first and second detectable compounds are distinguishable from each other.

6. The construct of claim 1, wherein said glioblastoma cells comprise U138 glioblastoma cell lines having a p53 and/or EGFR mutation; U373 glioblastoma cell lines having a p53 and/or EGFR mutation; U87 glioblastoma cell lines having a CDKN2A, NF1, and/or PTEN mutation; A172 glioblastoma cell lines having a CDKN2A, PTEN, and/or EGFR mutation; and/or U87 glioblastoma cell lines having a EGFR VIII deletion mutation.

7. The construct of claim 1, wherein said glioblastoma cells are from a glioblastoma cell line that is selected from glioblastoma cell lines having at least one mutation in a TP53 gene, IDH1 gene, IDH2 gene, PDGFRA gene, NF1 tumor suppressor gene, and/or PTEN gene.

8. The construct of claim 1, wherein a ratio of said glioblastoma cells to said first population of non-cancerous tissue cells in the construct is in a range of about 1:1 to about 20:1.

9. The construct of claim 1, further comprising a non-natural hydrogel that has a stiffness of about 0.05 to about 50 kilo Pascals at room temperature and atmospheric pressure.

10. The construct of claim 9, wherein the non-natural hydrogel comprises collagenase and/or hyaluronidase.

11. An artificial multicellular organoid comprising:
    at least two tumor cells that are of the same tissue type, but are distinct from one another; and
    non-cancerous tissue cells, wherein the non-cancerous tissue cells comprise astrocytes, glial cells, and endothelial cells,
    wherein the at least two tumor cells are brain tumor cells and are different glioblastoma subtypes or are representative of different glioblastoma subtypes, and
    wherein the at least two tumor cells and one or more of the non-cancerous tissue cells are intermixed with one another in the artificial multicellular organoid.

12. A method of preparing the artificial multicellular organoid of claim 11, the method comprising: encapsulating the at least two tumor cells and the non-cancerous tissue cells in a non-natural hydrogel, thereby preparing the artificial multicellular organoid.

13. A method of using the artificial cell construct of claim 1, the method comprising:
    administering a compound to the construct; and
    detecting a physiological, pharmacological, and/or toxicological response of the glioblastoma cells and/or non-cancerous tissue cells in the construct to the compound.

14. A method of screening a test compound and/or of monitoring cell and/or tumor behavior, the method comprising:
    providing the artificial cell construct of claim 1;
    contacting at least one test compound to the construct; and
    determining growth, metastasis, and/or amount of the glioblastoma cells and/or non-cancerous tissue cells in the construct after contact with the at least one test compound.

15. The construct of claim 1, wherein the construct further comprises stem cells.

16. The construct of claim 1, wherein the glioblastoma cells are patient biopsy-derived tumor cells.

17. The construct of claim 1, wherein the glioblastoma cells comprise cells representative of one or more glioblastoma subtypes that are selected from proneural, neural, classical, and mesenchymal.

18. The construct of claim 1, wherein a ratio of said glioblastoma cells to said first population of non-cancerous tissue cells in the construct is in a range of about 4:1 to about 16:1.

19. The multicellular organoid of claim 11, wherein the multicellular organoid comprises a core and a shell that surrounds the core, wherein the core comprises the at least two tumor cells, the astrocytes, and the glial cells, and the shell comprises the endothelial cells.

* * * * *

UNITED STATES PATENT AND TRADEMARK OFFICE
CERTIFICATE OF CORRECTION

| | | |
|---|---|---|
| PATENT NO. | : 11,959,095 B2 | Page 1 of 1 |
| APPLICATION NO. | : 16/341525 | |
| DATED | : April 16, 2024 | |
| INVENTOR(S) | : Skardal et al. | |

It is certified that error appears in the above-identified patent and that said Letters Patent is hereby corrected as shown below:

In the Specification

Column 7, Line 11: Please correct "0. 1%" to read --±0.1%--

Columns 27-28, TABLE 1 – continued: Please correct "Crosslinker 2 Endpoint G'" to read --Crosslinker 2--

Signed and Sealed this
Twentieth Day of August, 2024

Katherine Kelly Vidal
*Director of the United States Patent and Trademark Office*